(12) United States Patent
Vedantam et al.

(10) Patent No.: US 11,839,649 B2
(45) Date of Patent: Dec. 12, 2023

(54) COMPOSITIONS COMPRISING RECOMBINANT PROBIOTIC BACTERIA AND METHODS OF USE THEREOF

(71) Applicants: ARIZONA BOARD OF REGENTS ON BEHALF OF THE UNIVERSITY OF ARIZONA, Tucson, AZ (US); The United States Government as represented by the Department of Veterans Affairs, Washington, DC (US)

(72) Inventors: Gayatri Vedantam, Tucson, AZ (US); Virinchipuram K. Viswanathan, Tucson, AZ (US); Michael Mallozzi, Tucson, AZ (US)

(73) Assignees: ARIZONA BOARD OF REGENTS ON BEHALF OF THE UNIVERSITY OF ARIZONA, Tucson, AZ (US); The United States Government as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 17/155,923

(22) Filed: Jan. 22, 2021

(65) Prior Publication Data
US 2021/0205431 A1 Jul. 8, 2021

Related U.S. Application Data

(63) Continuation of application No. 16/813,131, filed on Mar. 9, 2020, now abandoned, which is a continuation of application No. 15/545,462, filed as application No. PCT/US2016/014590 on Jan. 22, 2016, now Pat. No. 10,583,186.

(60) Provisional application No. 62/107,224, filed on Jan. 23, 2015.

(51) Int. Cl.
  *A61K 39/08* (2006.01)
  *A61K 35/747* (2015.01)
  *A61K 39/00* (2006.01)
(52) U.S. Cl.
  CPC ............ *A61K 39/08* (2013.01); *A61K 35/747* (2013.01); *A61K 2039/523* (2013.01)
(58) Field of Classification Search
  None
  See application file for complete search history.

(56) References Cited

U.S. PATENT DOCUMENTS

2005/0233408 A1 10/2005 Pouwels et al.

FOREIGN PATENT DOCUMENTS

| WO | 9632486 | 10/1996 | | |
| WO | WO-2004046346 A2 * | 6/2004 | ........... | A61K 35/747 |

OTHER PUBLICATIONS

Meng et al. EMBO J Apr. 3, 2000; 19(7):1555-1566.*
Uniprot Accession #Q9AEM4, Jun. 1, 2001.
Karjalainen, T. et al. "Molecular and Genomic Analysis of Genes Encoding . . . " Infect. Immun. 69: 3442-3446 (May 2001).
International Search Report and Written Opinion for PCT International Application No. PCT/US16/14590 dated May 19, 2016.
UniProt Accession No. Q1JU94, S-layer protein Jun. 13, 2006 Retrieved on May 3, 2016, Retrieved from the internet <http://www.uniprot.org/uniprot/Q1JU94>.
NCBI Accession No. CAJ69681, Feb. 6, 2015.
NCBI Accession No. WP_011254065, May 15, 2013.
Duong, et al. "Construction of vectors for inducible and constitutive gene expression in Lactobacillus" Microb Biotechnol. 4(3), 2011, 357-367.
Ferreira, et al. "Immunization of mice with Lactobacillus casei expressing intimin fragments . . . " FEMS Immunol Med Microbiol. 54(2), 2008, 245-254.
Gaspar, et al. "Engineering Lactococcus lactis for production of mannitol: high yields from food-grade strains . . . " Appl Environ Microbiol. 70(3), 2004, 1466-1474.
Leenhouts, et al. "Campell-like integration of heterologous plasmid DNA into the chromosome of *Lactococcus lactis* subsp. lactis", Appl Environ Microbiol. 55(2), 1989, 394-400.
Merrigan, et al. "Surface-layer protein A (SlpA) is a major contributor to host-cell adherence of Clostridium difficile", PLoS One. 8(11), 2013, e78404.

* cited by examiner

*Primary Examiner* — Oluwatosin A Ogunbiyi
(74) *Attorney, Agent, or Firm* — Casimir Jones, S.C.; J. Mitchell Jones

(57) ABSTRACT

The invention features probiotic bacteria expressing *Clostridium difficile* SlpA, or fragment thereof, and its use for the treatment or prevention of *Clostridium difficile* infection and gut colonization.

8 Claims, 26 Drawing Sheets

Specification includes a Sequence Listing.

FIG. 1C

⭐ 1338 BP codon-optimized synthesized slpA chimera fragment

GGATCCATGAAGAAAAATTTAAGAATCGTTAGCGCTGCTGCTGCTGCTTTACTTGCTGTTGCTCCA
GTTGCTGCTTCTGCTGTATCTACTGTTAGCGCTGCTGCACCTGTATTTGCTGCAACCACTGGTACAC
AAGGCTATACGGTGGTTAAGAATGATTGGAAAAAGGCTGTCAAACAATTACAAGATGGACTTAAA
GATAATAGTATTGGTAAGATTACGGTCAGTTTCAATGATGGTGTGGTAGGAGAAGTAGCACCTAAA
TCAGCGAATAAGAAAGCAGATCGAGATGCAGCCGCAGAAAAGTTGTATAATCTTGTAAATACACAA
TTAGACAAATTAGGCGATGGCGATTATGTAGATTTTTCTGTTGATTACAATCTAGAGAATAAGATTAT
CACCAATCAAGCCGATGCCGAAGCTATTGTTACTAAATTGAATTCGTTAAATGAAAAGACGCTAATT
GATATTGCAACTAAAGATACGTTTGGAATGGTGTCTAAAACGCAGGATTCTGAAGGAAAGAATGTT
GCGGCAACAAAAGCGTTAAAAGTAAAAGATGTGGCAACTTTTGGCTTAAAGAGTGGAGGTAGTG
AAGATACCGGATATGTTGTCGAAATGAAAGCGGGTGCTGTTGAAGATAAGTATGGTAAAGTAGGT
GATTCTACAGCTGGTATTGCAATCAATCTTCCATCAACAGGTTTAGAATATGCAGGCAAAGGAACA
ACTATTGATTTCAACAAAACCCTTAAAGTTGATGTAACTGGTGGTAGTACACCGAGTGCAGTTGCC
GTAAGTGGGTTTGTGACTAAAGATGATACAGATTTAGCATCAAATACTAATGGTAAGTCAGCTACTT
TGCCAGTAGTTGTTACTGTTCCTAATGTTGCTGAGCCAACTGTAGCCAGCGTAAGCAAGAGAATTA
TGCACAACGCATACTACTACGACAAGGACGCTAAGCGTGTTGGTACTGACAGCGTTAAGCGTTACA
ACTCAGTAAGCGTATTGCCAAACACTACTACTATCAACGGTAAGACTTACTACCAAGTAGTTGAAAA
CGGTAAGGCTGTTGACAAGTACATCAACGCTGCAAACATCGATGGTACTAAGCGTACTTTGAAGCA
CAACGCTTACGTTTACGCATCATCAAAGAAGCGTGCTAACAAGGTTGTATTGAAGAAGGGTGAAG
TTGTAACTACTTACGGTGCTTCATACACATTCAAGAACGGCCAAAAGTACTACAAGATCGGTGACA
ACACTGACAAGACTTACGTTAAGGTTGCAAACTTTAGATAATAAAGATCTTCGCGGCCGCATCACT
AGTGAATTCGCGGCCGC (SEQ ID NO: 9)

FIG. 1D

TRANSLATED SlpA chimera fragment

```
MKKNLRIVSAAAAALLAVAPVAASAVSTVSAAAPVEAATTGTQGYTVVKN      50
DWKKAVKQLQDGLKDNSIGKITVSFNDGVVGEVAPKSANKKADRDAAAEK     100
LYNLVNTQLDKLGDGDYVDFSVDYNLENKIITNQADAEAIVTKLNSLNEK     150
TLIDIATKDTFGMVSKTQDSEGKNVAATKALKVKDVATFGLKSGGSEDTG     200
YVVEMKAGAVEDKYGKVGDSTAGIAINLPSTGLEYAGKGTTIDFNKTLKV     250
DVTGGSTPSAVAVSGFVTKDDTDLASNINGKSATLPVVVTVPNVAEPTVA     300
SVSKRIMHNAYYYDKDAKRVGTDSVKRYNSVSVLPNTTTINGKTYYQVVE     350
NGKAVDKYINAANIDGTKRTLKHNAYVYASSKKRANKVVLKKGEVVTTYG     400
ASYTFKNGQKYYKIGDNTDKTYVKVANFR*
```
(SEQ ID NO: 4)

Recombinant Lactobacillus expresses *C. difficile* SlpA protein on its surface

- Syrian Golden hamsters are safely and robustly colonized by recombinant Lactobacillus sp.

- Recombinant Lactobacillus protects hamsters from virulent *C. difficile* challenge

FIG. 6

**Construct 1: *Lactobacillus casei* single-integration system (DNA sequence)**

L. casei camp int (3166 bp)

FIG. 6 (CONTINUED)

*L. casei camp int (3166 bp) (from 1071-2140 bp)*

[Illegible sequence image - nucleotide sequence from positions ~1,080 to ~2,140 with restriction site annotations including PvuII, ClaI, ScaI, and PvuII]

FIG. 6 (CONTIUED)

*L. casei* double cross (3667 bp) (from 2830-3667 bp)

[sequence alignment figure with nucleotide positions 2,900 through 3,660]

(SEQ ID NO: 23)
(SEQ ID NO: 24)

FIG. 8

Construct 3: *Lactobacillus acidophilus* single-integration system (DNA sequence)

LA slpA Chi (3166 bp)

LA slpA Chi (3166 bp) (from 3104-3166 bp)

```
                                    PvuII      EcoRV    PmeI
GTGCTTCCGATTATGTAAAAAGATCCCGCTCACCCAGCTGGATCTTTCAGATATCGTTTAAAC  (SEQ ID NO: 25)
CACGAAGGCTAATACATTTTTCTAGGGCGAGTGGGTCGACCTAGAAAGTCTATAGCAAATTTG  (SEQ ID NO: 26)
     3,110     3,120    3,130    3,140    3,150    3,160
```

FIG. 9

> Construct 4: *Lactobacillus acidophilus* double-crossover integration system (DNA sequence)

LA slpA double cross (3720 bp)

LA slpA double cross (3720 bp) (from 3104-3720 bp)

[sequence illegible] (SEQ ID NO: 27)
[sequence illegible] (SEQ ID NO: 28)

SEQUENCE LISTING

<160> NUMBER OF SEQ ID NOS: 28

<210> SEQ ID NO 1
<211> LENGTH: 244
<212> TYPE: PRT
<213> ORGANISM: Clostridium difficile

<400> SEQUENCE: 1

```
Ala Ala Pro Val Phe Ala Ala Thr Thr Gly Thr Gln Gly Tyr Thr Val
1               5                   10                  15

Val Lys Asn Asp Trp Lys Lys Ala Val Lys Gln Leu Gln Asp Gly Leu
            20                  25                  30

Lys Asp Asn Ser Ile Gly Lys Ile Thr Val Ser Phe Asn Asp Gly Val
        35                  40                  45

Val Gly Glu Val Ala Pro Lys Ser Ala Asn Lys Lys Ala Asp Arg Asp
    50                  55                  60

Ala Ala Ala Glu Lys Leu Tyr Asn Leu Val Asn Thr Gln Leu Asp Lys
```

```
            65                  70                  75                  80
Leu Gly Asp Gly Asp Tyr Val Asp Phe Ser Val Asp Tyr Asn Leu Glu
                    85                  90                  95

Asn Lys Ile Ile Thr Asn Gln Ala Asp Ala Glu Ala Ile Val Thr Lys
                100                 105                 110

Leu Asn Ser Leu Asn Glu Lys Thr Leu Ile Asp Ile Ala Thr Lys Asp
            115                 120                 125

Thr Phe Gly Met Val Ser Lys Thr Gln Asp Ser Glu Gly Lys Asn Val
130                 135                 140

Ala Ala Thr Lys Ala Leu Lys Val Lys Asp Val Ala Thr Phe Gly Leu
145                 150                 155                 160

Lys Ser Gly Gly Ser Glu Asp Thr Gly Tyr Val Val Glu Met Lys Ala
                165                 170                 175

Gly Ala Val Glu Asp Lys Tyr Gly Lys Val Gly Asp Ser Thr Ala Gly
                180                 185                 190

Ile Ala Ile Asn Leu Pro Ser Thr Gly Leu Glu Tyr Ala Gly Lys Gly
            195                 200                 205

Thr Thr Ile Asp Phe Asn Lys Thr Leu Lys Val Asp Val Thr Gly Gly
            210                 215                 220

Ser Thr Pro Ser Ala Val Ala Val Ser Gly Phe Val Thr Lys Asp Asp
225                 230                 235                 240

Thr Asp Leu Ala

<210> SEQ ID NO 2
<211> LENGTH: 154
<212> TYPE: PRT
<213> ORGANISM: Lactobacillus acidophilus

<400> SEQUENCE: 2

Ser Asn Thr Asn Gly Lys Ser Ala Thr Leu Pro Val Val Thr Val
1               5                   10                  15

Pro Asn Val Ala Glu Pro Thr Val Ala Ser Val Ser Lys Arg Ile Met
                20                  25                  30

His Asn Ala Tyr Tyr Asp Lys Asp Ala Lys Arg Val Gly Thr Asp
            35                  40                  45

Ser Val Lys Arg Tyr Asn Ser Val Ser Val Leu Pro Asn Thr Thr Thr
50                  55                  60

Ile Asn Gly Lys Thr Tyr Tyr Gln Val Val Glu Asn Gly Lys Ala Val
65                  70                  75                  80

Asp Lys Tyr Ile Asn Ala Ala Asn Ile Asp Gly Thr Lys Arg Thr Leu
                85                  90                  95

Lys His Asn Ala Tyr Val Tyr Ala Ser Ser Lys Lys Arg Ala Asn Lys
                100                 105                 110

Val Val Leu Lys Lys Gly Glu Val Val Thr Thr Tyr Gly Ala Ser Tyr
            115                 120                 125

Thr Phe Lys Asn Gly Gln Lys Tyr Tyr Lys Ile Gly Asp Asn Thr Asp
130                 135                 140

Lys Thr Tyr Val Lys Val Ala Asn Phe Arg
145                 150

<210> SEQ ID NO 3
<211> LENGTH: 31
<212> TYPE: PRT
<213> ORGANISM: Lactobacillus acidophilus

<400> SEQUENCE: 3
```

Met Lys Lys Asn Leu Arg Ile Val Ser Ala Ala Ala Ala Leu Leu
1               5                   10                  15

Ala Val Ala Pro Val Ala Ala Ser Ala Val Ser Thr Val Ser Ala
            20                  25                  30

<210> SEQ ID NO 4
<211> LENGTH: 429
<212> TYPE: PRT
<213> ORGANISM: Artificial Sequence
<220> FEATURE:
<223> OTHER INFORMATION: SlpA Chimeric protein

<400> SEQUENCE: 4

Met Lys Lys Asn Leu Arg Ile Val Ser Ala Ala Ala Ala Leu Leu
1               5                   10                  15

Ala Val Ala Pro Val Ala Ala Ser Ala Val Ser Thr Val Ser Ala Ala
            20                  25                  30

Ala Pro Val Phe Ala Ala Thr Thr Gly Thr Gln Gly Tyr Thr Val Val
                35                  40                  45

Lys Asn Asp Trp Lys Lys Ala Val Lys Gln Leu Gln Asp Gly Leu Lys
    50                  55                  60

Asp Asn Ser Ile Gly Lys Ile Thr Val Ser Phe Asn Asp Gly Val Val
65                  70                  75                  80

Gly Glu Val Ala Pro Lys Ser Ala Asn Lys Lys Ala Asp Arg Asp Ala
                85                  90                  95

Ala Ala Glu Lys Leu Tyr Asn Leu Val Asn Thr Gln Leu Asp Lys Leu
                100                 105                 110

Gly Asp Gly Asp Tyr Val Asp Phe Ser Val Asp Tyr Asn Leu Glu Asn
            115                 120                 125

Lys Ile Ile Thr Asn Gln Ala Asp Ala Glu Ala Ile Val Thr Lys Leu
    130                 135                 140

Asn Ser Leu Asn Glu Lys Thr Leu Ile Asp Ile Ala Thr Lys Asp Thr
145                 150                 155                 160

Phe Gly Met Val Ser Lys Thr Gln Asp Ser Glu Gly Lys Asn Val Ala
                165                 170                 175

Ala Thr Lys Ala Leu Lys Val Lys Asp Val Ala Thr Phe Gly Leu Lys
                180                 185                 190

Ser Gly Gly Ser Glu Asp Thr Gly Tyr Val Val Glu Met Lys Ala Gly
            195                 200                 205

Ala Val Glu Asp Lys Tyr Gly Lys Val Gly Asp Ser Thr Ala Gly Ile
    210                 215                 220

Ala Ile Asn Leu Pro Ser Thr Gly Leu Glu Tyr Ala Gly Lys Gly Thr
225                 230                 235                 240

Thr Ile Asp Phe Asn Lys Thr Leu Lys Val Asp Val Thr Gly Gly Ser
                245                 250                 255

Thr Pro Ser Ala Val Ala Val Ser Gly Phe Val Thr Lys Asp Asp Thr
            260                 265                 270

Asp Leu Ala Ser Asn Thr Asn Gly Lys Ser Ala Thr Leu Pro Val Val
    275                 280                 285

Val Thr Val Pro Asn Val Ala Glu Pro Thr Val Ala Ser Val Ser Lys
290                 295                 300

Arg Ile Met His Asn Ala Tyr Tyr Asp Lys Asp Ala Lys Arg Val
305                 310                 315                 320

Gly Thr Asp Ser Val Lys Arg Tyr Asn Ser Val Ser Val Leu Pro Asn
            325                 330                 335

Thr Thr Thr Ile Asn Gly Lys Thr Tyr Tyr Gln Val Glu Asn Gly
         340                 345                 350

Lys Ala Val Asp Lys Tyr Ile Asn Ala Ala Asn Ile Asp Gly Thr Lys
             355                 360                 365

Arg Thr Leu Lys His Asn Ala Tyr Val Tyr Ala Ser Ser Lys Lys Arg
    370                 375                 380

Ala Asn Lys Val Val Leu Lys Lys Gly Glu Val Thr Thr Tyr Gly
385                 390                 395                 400

Ala Ser Tyr Thr Phe Lys Asn Gly Gln Lys Tyr Tyr Lys Ile Gly Asp
                405                 410                 415

Asn Thr Asp Lys Thr Tyr Val Lys Val Ala Asn Phe Arg
            420                 425

<210> SEQ ID NO 5
<211> LENGTH: 1323
<212> TYPE: DNA
<213> ORGANISM: Artificial Sequence
<220> FEATURE:
<223> OTHER INFORMATION: SlpA Chimeric gene

<400> SEQUENCE: 5

```
ggatccatga agaaaaattt aagaatcgtt agcgctgctg ctgctgcttt acttgctgtt      60
gctccagttg ctgcttctgc tgtatctact gttagcgctg ctgcacctgt atttgctgca     120
accactggta cacaaggcta cggtggttgt aagaatgatt ggaaaaaggc tgtcaaacaa     180
ttacaagatg gacttaaaga taatagtatt ggtaagatta cggtcagttt caatgatggt     240
gtggtaggag aagtagcacc taaatcagcg aataagaaag cagatcgaga tgcagccgca     300
gaaaagttgt ataatcttgt aaatacacaa ttagacaaat taggcgatgg cgattatgta     360
gatttttctg ttgattacaa tctagagaat aagattatca ccaatcaagc cgatgccgaa     420
gctattgtta ctaaattgaa ttcgttaaat gaaagacgc taattgatat tgcaactaaa     480
gatacgtttg gaatggtgtc taaaacgcag gattctgaag aaagaatgt tgcggcaaca     540
aaagcgttaa agtaaaaaga tgtggcaact tttggcttaa agagtggagg tagtgaagat     600
accggatatg ttgtcgaaat gaaagcgggt gctgttgaag ataagtatgg taaagtaggt     660
gattctacag ctggtattgc aatcaatctt ccatcaacag gtttagaata tgcaggcaaa     720
ggaacaacta ttgatttcaa caaaacccct aaagttgatg taactggtgg tagtacaccg     780
agtgcagttg ccgtaagtgg gtttgtgact aaagatgata cagatttagc atcaaatact     840
aatggtaagt cagctacttt gccagtagtt gttactgttc ctaatgttgc tgagccaact     900
gtagccagcg taagcaagag aattatgcac aacgcatact actacgacaa ggacgctaag     960
cgtgttggta ctgacagcgt taagcgttac aactcagtaa gcgtattgcc aaacactact    1020
actatcaacg gtaagactta ctaccaagta gttgaaaacg gtaaggctgt tgacaagtac    1080
atcaacgctg caaacatcga tggtactaag cgtactttga gcacaacgc ttacgtttac    1140
gcatcatcaa agaagcgtgc taacaaggtt gtattgaaga agggtgaagt tgtaactact    1200
tacggtgctt catacacatt caagaacggc caaaagtact acaagatcgg tgacaacact    1260
gacaagactt acgttaaggt tgcaaacttt agataataaa gatcttcgaa ttcccgcggc    1320
cgc                                                                  1323
```

<210> SEQ ID NO 6
<211> LENGTH: 719
<212> TYPE: PRT

<213> ORGANISM: Clostridium difficile

<400> SEQUENCE: 6

```
Met Asn Lys Lys Asn Ile Ala Ile Ala Met Ser Gly Leu Thr Val Leu
1               5                   10                  15

Ala Ser Ala Ala Pro Val Phe Ala Ala Thr Thr Gly Thr Gln Gly Tyr
            20                  25                  30

Thr Val Val Lys Asn Asp Trp Lys Lys Ala Val Lys Gln Leu Gln Asp
        35                  40                  45

Gly Leu Lys Asp Asn Ser Ile Gly Lys Ile Thr Val Ser Phe Asn Asp
    50                  55                  60

Gly Val Val Gly Glu Val Ala Pro Lys Ser Ala Asn Lys Lys Ala Asp
65                  70                  75                  80

Arg Asp Ala Ala Ala Glu Lys Leu Tyr Asn Leu Val Asn Thr Gln Leu
                85                  90                  95

Asp Lys Leu Gly Asp Gly Asp Tyr Val Asp Phe Ser Val Asp Tyr Asn
            100                 105                 110

Leu Glu Asn Lys Ile Ile Thr Asn Gln Ala Asp Ala Glu Ala Ile Val
        115                 120                 125

Thr Lys Leu Asn Ser Leu Asn Glu Lys Thr Leu Ile Asp Ile Ala Thr
130                 135                 140

Lys Asp Thr Phe Gly Met Val Ser Lys Thr Gln Asp Ser Glu Gly Lys
145                 150                 155                 160

Asn Val Ala Ala Thr Lys Ala Leu Lys Val Lys Asp Val Ala Thr Phe
                165                 170                 175

Gly Leu Lys Ser Gly Gly Ser Glu Asp Thr Gly Tyr Val Val Glu Met
            180                 185                 190

Lys Ala Gly Ala Val Glu Asp Lys Tyr Gly Lys Val Gly Asp Ser Thr
        195                 200                 205

Ala Gly Ile Ala Ile Asn Leu Pro Ser Thr Gly Leu Glu Tyr Ala Gly
    210                 215                 220

Lys Gly Thr Thr Ile Asp Phe Asn Lys Thr Leu Lys Val Asp Val Thr
225                 230                 235                 240

Gly Gly Ser Thr Pro Ser Ala Val Ala Val Ser Gly Phe Val Thr Lys
                245                 250                 255

Asp Asp Thr Asp Leu Ala Lys Ser Gly Thr Ile Asn Val Arg Val Ile
            260                 265                 270

Asn Ala Lys Glu Glu Ser Ile Asp Ile Asp Ala Ser Ser Tyr Thr Ser
        275                 280                 285

Ala Glu Asn Leu Ala Lys Arg Tyr Val Phe Asp Pro Asp Glu Ile Ser
    290                 295                 300

Glu Ala Tyr Lys Ala Ile Val Ala Leu Gln Asn Asp Gly Ile Glu Ser
305                 310                 315                 320

Asn Leu Val Gln Leu Val Asn Gly Lys Tyr Gln Val Ile Phe Tyr Pro
                325                 330                 335

Glu Gly Lys Arg Leu Glu Thr Lys Ser Ala Asn Asp Thr Ile Ala Ser
            340                 345                 350

Gln Asp Thr Pro Ala Lys Val Val Ile Lys Ala Asn Lys Leu Lys Asp
        355                 360                 365

Leu Lys Asp Tyr Val Asp Asp Leu Lys Thr Tyr Asn Asn Thr Tyr Ser
    370                 375                 380

Asn Val Val Thr Val Ala Gly Glu Asp Arg Ile Glu Thr Ala Ile Glu
385                 390                 395                 400
```

```
Leu Ser Ser Lys Tyr Tyr Asn Ser Asp Asp Lys Asn Ala Ile Thr Asp
            405                 410                 415

Lys Ala Val Asn Asp Ile Val Leu Val Gly Ser Thr Ser Ile Val Asp
            420                 425                 430

Gly Leu Val Ala Ser Pro Leu Ala Ser Glu Lys Thr Ala Pro Leu Leu
            435                 440                 445

Leu Thr Ser Lys Asp Lys Leu Asp Ser Ser Val Lys Ser Glu Ile Lys
450                 455                 460

Arg Val Met Asn Leu Lys Ser Asp Thr Gly Ile Asn Thr Ser Lys Lys
465                 470                 475                 480

Val Tyr Leu Ala Gly Gly Val Asn Ser Ile Ser Lys Asp Val Glu Asn
            485                 490                 495

Glu Leu Lys Asn Met Gly Leu Lys Val Thr Arg Leu Ser Gly Glu Asp
            500                 505                 510

Arg Tyr Glu Thr Ser Leu Ala Ile Ala Asp Glu Ile Gly Leu Asp Asn
            515                 520                 525

Asp Lys Ala Phe Val Val Gly Gly Thr Gly Leu Ala Asp Ala Met Ser
            530                 535                 540

Ile Ala Pro Val Ala Ser Gln Leu Lys Asp Gly Asp Ala Thr Pro Ile
545                 550                 555                 560

Val Val Val Asp Gly Lys Ala Lys Glu Ile Ser Asp Ala Lys Ser
            565                 570                 575

Phe Leu Gly Thr Ser Asp Val Asp Ile Ile Gly Gly Lys Asn Ser Val
            580                 585                 590

Ser Lys Glu Ile Glu Glu Ser Ile Asp Ser Ala Thr Gly Lys Thr Pro
            595                 600                 605

Asp Arg Ile Ser Gly Asp Asp Arg Gln Ala Thr Asn Ala Glu Val Leu
            610                 615                 620

Lys Glu Asp Asp Tyr Phe Thr Asp Gly Glu Val Val Asn Tyr Phe Val
625                 630                 635                 640

Ala Lys Asp Gly Ser Thr Lys Glu Asp Gln Leu Val Asp Ala Leu Ala
            645                 650                 655

Ala Ala Pro Ile Ala Gly Arg Phe Lys Glu Ser Pro Ala Pro Ile Ile
            660                 665                 670

Leu Ala Thr Asp Thr Leu Ser Ser Asp Gln Asn Val Ala Val Ser Lys
            675                 680                 685

Ala Val Pro Lys Asp Gly Gly Thr Asn Leu Val Gln Val Gly Lys Gly
            690                 695                 700

Ile Ala Ser Ser Val Ile Asn Lys Met Lys Asp Leu Leu Asp Met
705                 710                 715

<210> SEQ ID NO 7
<211> LENGTH: 444
<212> TYPE: PRT
<213> ORGANISM: Lactobacillus acidophilus

<400> SEQUENCE: 7

Met Lys Lys Asn Leu Arg Ile Val Ser Ala Ala Ala Ala Leu Leu
1               5                   10                  15

Ala Val Ala Pro Val Ala Ala Ser Ala Val Ser Val Ser Ala Ala
            20                  25                  30

Thr Thr Ile Asn Ala Ser Ser Ser Ala Ile Asn Thr Asn Thr Asn Ala
            35                  40                  45

Lys Tyr Asp Val Asp Val Thr Pro Ser Val Ser Ala Val Ala Ala Asn
50                  55                  60
```

```
Thr Ala Asn Asn Thr Pro Ala Ile Ala Gly Asn Leu Thr Gly Thr Ile
 65                  70                  75                  80

Ser Ala Ser Tyr Asn Gly Lys Thr Tyr Thr Ala Asn Leu Lys Ala Asp
             85                  90                  95

Thr Glu Asn Ala Thr Ile Thr Ala Ala Gly Ser Thr Thr Ala Val Lys
            100                 105                 110

Pro Ala Glu Leu Ala Ala Gly Val Ala Tyr Thr Val Thr Val Asn Asp
            115                 120                 125

Val Ser Phe Asn Phe Gly Ser Glu Asn Ala Gly Lys Thr Val Thr Leu
130                 135                 140

Gly Ser Ala Asn Ser Asn Val Lys Phe Thr Gly Thr Asn Ser Asp Asn
145                 150                 155                 160

Gln Thr Glu Thr Asn Val Ser Thr Leu Lys Val Lys Leu Asp Gln Asn
            165                 170                 175

Gly Val Ala Ser Leu Thr Asn Val Ser Ile Ala Asn Val Tyr Ala Ile
            180                 185                 190

Asn Thr Thr Asp Asn Ser Asn Val Asn Phe Tyr Asp Val Thr Ser Gly
            195                 200                 205

Ala Thr Val Thr Asn Gly Ala Val Ser Val Asn Ala Asp Asn Gln Gly
            210                 215                 220

Gln Val Asn Val Ala Asn Val Val Ala Ile Asn Ser Lys Tyr Phe
225                 230                 235                 240

Ala Ala Gln Tyr Ala Asp Lys Lys Leu Asn Thr Arg Thr Ala Asn Thr
            245                 250                 255

Glu Asp Ala Ile Lys Ala Ala Leu Lys Asp Gln Lys Ile Asp Val Asn
            260                 265                 270

Ser Val Gly Tyr Phe Lys Ala Pro His Thr Phe Thr Val Asn Val Lys
            275                 280                 285

Ala Thr Ser Asn Thr Asn Gly Lys Ser Ala Thr Leu Pro Val Val Val
            290                 295                 300

Thr Val Pro Asn Val Ala Glu Pro Thr Val Ala Ser Val Ser Lys Arg
305                 310                 315                 320

Ile Met His Asn Ala Tyr Tyr Tyr Asp Lys Asp Ala Lys Arg Val Gly
            325                 330                 335

Thr Asp Ser Val Lys Arg Tyr Asn Ser Val Ser Val Leu Pro Asn Thr
            340                 345                 350

Thr Thr Ile Asn Gly Lys Thr Tyr Tyr Gln Val Val Glu Asn Gly Lys
            355                 360                 365

Ala Val Asp Lys Tyr Ile Asn Ala Ala Asn Ile Asp Gly Thr Lys Arg
            370                 375                 380

Thr Leu Lys His Asn Ala Tyr Val Tyr Ala Ser Ser Lys Lys Arg Ala
385                 390                 395                 400

Asn Lys Val Val Leu Lys Lys Gly Glu Val Val Thr Thr Tyr Gly Ala
            405                 410                 415

Ser Tyr Thr Phe Lys Asn Gly Gln Tyr Tyr Lys Ile Gly Asp Asn
            420                 425                 430

Thr Asp Lys Thr Tyr Val Lys Val Ala Asn Phe Arg
            435                 440
```

<210> SEQ ID NO 8
<211> LENGTH: 323
<212> TYPE: PRT
<213> ORGANISM: Clostridium difficile

<400> SEQUENCE: 8

Ala Gly Glu Asp Arg Ile Glu Thr Ala Ile Glu Leu Ser Ser Lys Tyr
1               5                   10                  15

Tyr Asn Ser Asp Asp Lys Asn Ala Ile Thr Asp Lys Ala Val Asn Asp
            20                  25                  30

Ile Val Leu Val Gly Ser Thr Ser Ile Val Asp Gly Leu Val Ala Ser
        35                  40                  45

Pro Leu Ala Ser Glu Lys Thr Ala Pro Leu Leu Thr Ser Lys Asp
    50                  55                  60

Lys Leu Asp Ser Ser Val Lys Ser Glu Ile Lys Arg Val Met Asn Leu
65              70                  75                  80

Lys Ser Asp Thr Gly Ile Asn Thr Ser Lys Lys Val Tyr Leu Ala Gly
            85                  90                  95

Gly Val Asn Ser Ile Ser Lys Asp Val Glu Asn Glu Leu Lys Asn Met
            100                 105                 110

Gly Leu Lys Val Thr Arg Leu Ser Gly Glu Asp Arg Tyr Glu Thr Ser
        115                 120                 125

Leu Ala Ile Ala Asp Glu Ile Gly Leu Asp Asn Asp Lys Ala Phe Val
    130                 135                 140

Val Gly Gly Thr Gly Leu Ala Asp Ala Met Ser Ile Ala Pro Val Ala
145                 150                 155                 160

Ser Gln Leu Lys Asp Gly Asp Ala Thr Pro Ile Val Val Asp Gly
            165                 170                 175

Lys Ala Lys Glu Ile Ser Asp Asp Ala Lys Ser Phe Leu Gly Thr Ser
            180                 185                 190

Asp Val Asp Ile Ile Gly Gly Lys Asn Ser Val Ser Lys Glu Ile Glu
        195                 200                 205

Glu Ser Ile Asp Ser Ala Thr Gly Lys Thr Pro Asp Arg Ile Ser Gly
    210                 215                 220

Asp Asp Arg Gln Ala Thr Asn Ala Glu Val Leu Lys Glu Asp Tyr
225                 230                 235                 240

Phe Thr Asp Gly Glu Val Val Asn Tyr Phe Val Ala Lys Asp Gly Ser
            245                 250                 255

Thr Lys Glu Asp Gln Leu Val Asp Ala Leu Ala Ala Pro Ile Ala
            260                 265                 270

Gly Arg Phe Lys Glu Ser Pro Ala Pro Ile Ile Leu Ala Thr Asp Thr
        275                 280                 285

Leu Ser Ser Asp Gln Asn Val Ala Val Ser Lys Ala Val Pro Lys Asp
    290                 295                 300

Gly Gly Thr Asn Leu Val Gln Val Gly Lys Gly Ile Ala Ser Ser Val
305                 310                 315                 320

Ile Asn Lys

<210> SEQ ID NO 9
<211> LENGTH: 1338
<212> TYPE: DNA
<213> ORGANISM: Artificial Sequence
<220> FEATURE:
<223> OTHER INFORMATION: SlpA Chimeric gene

<400> SEQUENCE: 9
ggatccatga agaaaaattt aagaatcgtt agcgctgctg ctgctgcttt acttgctgtt    60
gctccagttg ctgcttctgc tgtatctact gttagcgctg ctgcacctgt atttgctgca   120
accactggta cacaaggcta tacggtggtt aagaatgatt ggaaaaaggc tgtcaaacaa   180

```
ttacaagatg gacttaaaga taatagtatt ggtaagatta cggtcagttt caatgatggt      240
gtggtaggag aagtagcacc taaatcagcg aataagaaag cagatcgaga tgcagccgca      300
gaaaagttgt ataatcttgt aaatacacaa ttagacaaat taggcgatgg cgattatgta      360 gattttctg ttgattacaa tctagagaat aagattatca ccaatcaagc cgatgccgaa       420
gctattgtta ctaaattgaa ttcgttaaat gaaaagacgc taattgatat tgcaactaaa      480
gatacgtttg gaatggtgtc taaaacgcag gattctgaag gaaagaatgt tgcggcaaca      540
aaagcgttaa aagtaaaaga tgtggcaact tttggcttaa agagtggagg tagtgaagat      600
accggatatg ttgtcgaaat gaaagcgggt gctgttgaag ataagtatgg taaagtaggt      660
gattctacag ctggtattgc aatcaatctt ccatcaacag gtttagaata tgcaggcaaa      720
ggaacaacta ttgatttcaa caaaacccctt aaagttgatg taactggtgg tagtacaccg     780
agtgcagttg ccgtaagtgg gtttgtgact aaagatgata cagatttagc atcaaatact      840
aatggtaagt cagctacttt gccagtagtt gttactgttc ctaatgttgc tgagccaact      900
gtagccagcg taagcaagag aattatgcac aacgcatact actacgacaa ggacgctaag      960
cgtgttggta ctgacagcgt taagcgttac aactcagtaa gcgtattgcc aaacactact     1020
actatcaacg gtaagactta ctaccaagta gttgaaaacg gtaaggctgt tgacaagtac     1080
atcaacgctg caaacatcga tggtactaag cgtactttga agcacaacgc ttacgtttac     1140
gcatcatcaa agaagcgtgc taacaaggtt gtattgaaga agggtgaagt tgtaactact     1200
tacggtgctt catacacatt caagaacggc caaaagtact acaagatcgg tgacaacact     1260
gacaagactt acgttaaggt tgcaaacttt agataataaa gatcttcgcg gccgcatcac     1320
tagtgaattc gcggccgc                                                   1338

<210> SEQ ID NO 10
<211> LENGTH: 250
<212> TYPE: DNA
<213> ORGANISM: Lactobacillus acidophilus

<400> SEQUENCE: 10
tataaatggc aataccacaa ataactgtt gacaagttgt gaaagcgata ttatcattta       60
attgtaaatt gaaaacgttt ccaaagtgtt caaatagttt tttgctaaat aattattttt     120
ttgtagcgaa atagaaacgt ttcaattaat ttaaaacaat tagatcttag taggaaacct     180
tttaattttt gtgcaaaatt gaaacgtttc aaaaggagga aaatgaaaaa atggaaatt     240 aggagttgca                                                            250

<210> SEQ ID NO 11
<211> LENGTH: 7
<212> TYPE: PRT
<213> ORGANISM: Lactobacillus acidophilus

<400> SEQUENCE: 11

Ile Asn Gly Asn Thr Thr Lys
1               5

<210> SEQ ID NO 12
<211> LENGTH: 9
<212> TYPE: PRT
<213> ORGANISM: Lactobacillus acidophilus

<400> SEQUENCE: 12

Met Lys Lys Trp Lys Leu Gly Val Ala
```

<210> SEQ ID NO 13
<211> LENGTH: 250
<212> TYPE: DNA
<213> ORGANISM: Lactobacillus acidophilus

<400> SEQUENCE: 13

```
gttgtcatag ttaatttctt ttcttttttaa aaaacttact tacgtttatt atacaaaata    60
tttactcaat tccaataaat attaatttta gcaaaaacaa attttttaag aatcttcgta   120
ataaatattt tactgttttt agataaatat tttattttat tggttaattt tttatttggt   180
gatataataa aagcgttttc aaaaataatt tattatagaa atcaggtatt agtatgcaag   240
caaacataag                                                          250
```

<210> SEQ ID NO 14
<211> LENGTH: 5
<212> TYPE: PRT
<213> ORGANISM: Lactobacillus acidophilus

<400> SEQUENCE: 14

Met Gln Ala Asn Ile
1               5

<210> SEQ ID NO 15
<211> LENGTH: 250
<212> TYPE: DNA
<213> ORGANISM: Lactobacillus acidophilus

<400> SEQUENCE: 15

```
tcttgtgcaa taatgtctga ttttgattcc gtcatttatg tctttccttt ctttgtacat    60
ttattatatt cataaatgta tagacaagta aagcataatt taagttacta taagtaaat    120
attgtgatcg ctttcaaaaa atatattgac aacttgtata tacaagttta atataatagc   180
taaatctaat gaaaacgctt tatacaggag aaaaacaatg aatgaaaaca atgaaattgc   240
aattctcgct                                                          250
```

<210> SEQ ID NO 16
<211> LENGTH: 11
<212> TYPE: PRT
<213> ORGANISM: Lactobacillus acidophilus

<400> SEQUENCE: 16

Gln Ala Ile Ile Asp Ser Lys Ser Glu Thr Met
1               5                   10

<210> SEQ ID NO 17
<211> LENGTH: 11
<212> TYPE: PRT
<213> ORGANISM: Lactobacillus acidophilus

<400> SEQUENCE: 17

Met Asn Glu Asn Asn Glu Ile Ala Ile Leu Ala
1               5                   10

<210> SEQ ID NO 18
<211> LENGTH: 200
<212> TYPE: DNA
<213> ORGANISM: Lactobacillus acidophilus

<400> SEQUENCE: 18

```
ttttgtttttt catgattttt acacttctct tagtatgctt ttgttataag ttagcacaaa      60
aaagcagaaa ataaaaagta gaaataaaaa aagatgtttt tttgcccata tctctatgaa     120
aaaaactgtg aaatgtgtaa aatatggatg aaacattgaa tttaaaagga gatatttcat     180
gtcaaaatta gttttaatcc                                                 200
```

<210> SEQ ID NO 19
<211> LENGTH: 4
<212> TYPE: PRT
<213> ORGANISM: Lactobacillus acidophilus

<400> SEQUENCE: 19

Lys Asn Lys Met
1

<210> SEQ ID NO 20
<211> LENGTH: 7
<212> TYPE: PRT
<213> ORGANISM: Lactobacillus acidophilus

<400> SEQUENCE: 20

Met Ser Lys Leu Val Leu Ile
1               5

<210> SEQ ID NO 21
<211> LENGTH: 3166
<212> TYPE: DNA
<213> ORGANISM: Artificial Sequence
<220> FEATURE:
<223> OTHER INFORMATION: Polynucleotide for Lactobacillus integration

<400> SEQUENCE: 21

```
ggccggcctt ggtgctcaaa tgcgctttga cttatcaaaa gggtttccaa ttttaaccac      60
taaaaaggtt ccattcggtt taattaaaag tgaactccta tggttcttac gaggggacac     120
taatattcgt ttttttattag aacataaaaa tcatatttgg gatgagtggg catttaaaaa    180
ttgggttaac agtgatgaat atactggtcc tgatatgact gattttggtt tacgaagtca     240
aagtgatccg gaatttaata aaatttatca agctgaatta aaaaaatttg atcgacgtat     300
ccttgatgat gagaacttcg ccaaaaaata tggtaattta ggcgacgttt atggtgcaca     360
atggcgccat tggcaaaaagc gagatggtag ctttattgat caaattgaag atctattaga    420 cttcttttc ctccgatcat atgatcggag gaaaagaaa tctaatagtt ttacacttct       480
cttagtatgc ttttgttata agttagcaca aaaaagcaga aataaaaag tagaaataaa      540 aaagatgtt tttttgccca tatctctatg aaaaaaactg tgaaatgtgt aaaatatgga      600
tgaaacattg aatttaaaag gagatattat gaagaaaaat ttaagaatcg ttagcgctgc     660
tgctgctgct ttacttgctg ttgctccagt tgctgcttct gctgtatcta ctgttagcgc    720
tgctgcacct gtatttgctg caaccactgg tacacaaggc tatacggtgg ttaagaatga    780
ttggaaaaag gctgtcaaac aattacaaga tggacttaaa gataatagta ttggtaagat    840
tacggtcagt ttcaatgatg gtgtggtagg agaagtagca cctaaatcag cgaataagaa    900
agcagatcga gatgcagccg cagaaaaagtt gtataatctt gtaaatacac aattagacaa    960
attaggcgat ggcgattatg tagattttc tgttgattac aatctagaga ataagattat    1020
caccaatcaa gccgatgccg aagctattgt tactaaattg aattcgttaa atgaaaagac   1080
gctaattgat attgcaacta agatacgtt tggaatggtc tctaaaacgc aggattctga    1140
aggaaagaat gttgcggcaa caaaagcgtt aaaagtaaaa gatgtggcaa cttttggctt   1200
```

```
aaagagtgga ggtagtgaag ataccggata tgttgtcgaa atgaaagcgg gtgctgttga    1260
agataagtat ggtaaagtag gtgattctac agctggtatt gcaatcaatc ttccatcaac    1320
aggtttagaa tatgcaggca aaggaacaac tattgatttc aacaaaaccc ttaaagttga    1380
tgtaactggt ggtagtacac cgagtgcagt tgccgtaagt gggtttgtga ctaaagatga    1440
tacagattta gcatcaaata ctaatggtaa gtcagctact ttgccagtag ttgttactgt    1500
tcctaatgtt gctgagccaa ctgtagccag cgtaagcaag agaattatgc acaacgcata    1560
ctactacgac aaggacgcta agcgtgttgg tactgacagc gttaagcgtt acaactcagt    1620
aagcgtattg ccaaacacta ctactatcaa cggtaagact tactaccaag tagttgaaaa    1680
cggtaaggct gttgacaagt acatcaacgc tgcaaacatc gatggtacta agcgtacttt    1740
gaagcacaac gcttacgttt acgcatcatc aaagaagcgt gctaacaagg ttgtattgaa    1800
gaagggtgaa gttgtaacta cttacggtgc ttcatacaca ttcaagaacg ccaaaagta    1860 ctacaagatc ggtgacaaca ctgacaagac ttacgttaag gttgcaaact ttagataata    1920
agatcttatt aagattaccg ttatccgtga aaaacgagtg gtagcaattg ctaaataaca    1980
aaaagagtat gagttttttgc tcatactctt tttgttattt gtgcaaatac cgctctactt    2040
gtataattag aacaagtata taggaaagt agccgaatat gtttaaaatt attgttgaat    2100
tattcttatt agtaattatt tcagctgctc aattacgcca tttattagag ggcgcgcctg    2160
aggacaagcc ctaatgacaa acaacaaact gcacttgctt gaatcagaac atgtgttgtg    2220
ctacggttac tgtagaattc atttttaaaa aggggaatat caggctttcg catagcaagc    2280
tgacggccta agggggattt atatggctag ttttcaatca tttgggatac caggacagct    2340
ggaagtcatc aaaaaagcac ttgatcacgt gcgagtcggt gtggtaatta cagatcccgc    2400
acttgaagat aatcctattg tctacgtaaa tcaaggcttt gttcaaatga ccggctacga    2460
gaccgaggaa attttaggaa agaacgcacg cttcttacag gaaattttag gaaagaacgc    2520
acgcttctta caggggaaac acacagatcc tgcagaagtg gacaacatca gaaccgcttt    2580
acaaaataaa gaaccggtca ccgttcagat ccaaaactac aaaaaagacg aacgatgtt    2640 ctggaatgaa ttaaatattg atccaatgga aatagaggat aaaacgtatt ttgtcggaat    2700
tcagaatgat atcaccaagc aaaaagaata tgaaaagctt ctcgaggatt ccctcacgga    2760
aattactgca ctttcaactc ctattgtccc gattcgcaat ggcatttcgg ctcttccgct    2820
agtcggaaac ctgacagagg agcgatttaa ttccatcgtt tgcacattga cgaatatctt    2880
atcaacatcc aaagatgatt atttgatcat tgatttatcc ggattggccc aagtgaacga    2940
acaaacggcc gaccaaattt tcaagctgag ccatttgctg aaattgaccg gaactgagtt    3000
aatcattact ggcattaagc ctgaattggc tatgaaaatg aataaactgg atgccaattt    3060
ttcgtcgctg aaaacatatt caaatgtaaa ggatgccgtt aaagtgcttc cgattatgta    3120
aaaagatccc gctcacccag ctggatcttt cagatatcgt ttaaac    3166
```

<210> SEQ ID NO 22
<211> LENGTH: 3166
<212> TYPE: DNA
<213> ORGANISM: Artificial Sequence
<220> FEATURE:
<223> OTHER INFORMATION: Polynucleotide for Lactobacillus integration

<400> SEQUENCE: 22

```
gtttaaacga tatctgaaag atccagctgg gtgagcggga tcttttttaca taatcggaag    60
```

```
cactttaacg gcatccttta catttgaata tgttttcagc gacgaaaaat tggcatccag      120
tttattcatt ttcatagcca attcaggctt aatgccagta atgattaact cagttccggt      180
caatttcagc aaatggctca gcttgaaaat ttggtcggcc gtttgttcgt tcacttgggc      240
caatccggat aaatcaatga tcaaataatc atctttggat gttgataaga tattcgtcaa      300
tgtgcaaacg atggaattaa atcgctcctc tgtcaggttt ccgactagcg aagagccga      360 aatgccattg cgaatcggga cataggagt tgaaagtgca gtaatttccg tgagggaatc      420
ctcgagaagc ttttcatatt cttttttgctt ggtgatatca ttctgaattc cgacaaaata    480
cgttttatcc tctatttcca ttggatcaat atttaattca ttccagaaca tcgttccgtc     540
ttttttgtag ttttggatct gaacggtgac cggttcttta ttttgtaaag cggttctgat     600
gttgtccact tctgcaggat ctgtgtgttt ccctgtaag aagcgtgcgt tctttcctaa      660
aatttcctgt aagaagcgtg cgttctttcc taaaatttcc tcggtctcgt agccggtcat    720
ttgaacaaag ccttgattta cgtagacaat aggattatct tcaagtgcgg gatctgtaat    780
taccacaccg actcgcacgt gatcaagtgc tttttttgatg acttccagct gtcctggtat    840
cccaaatgat tgaaaactag ccatataaat ccccccttagg ccgtcagctt gctatgcgaa    900
agcctgatat tccccttttt aaaaatgaat tctacagtaa ccgtagcaca acacatgttc   960
tgattcaagc aagtgcagtt tgttgtttgt cattagggct tgtcctcagg cgcgccctct    1020
aataaatggc gtaattgagc agctgaaata attactaata agaataattc aacaataatt    1080
ttaaacatat tcggctactt tccttatata cttgttctaa ttataccagt agagcggtat    1140
ttgcacaaat aacaaaaaga gtatgagcaa aaactcatac tctttttgtt atttagcaat    1200
tgctaccact cgttttttcac ggataacggt aatcttaata agatcttatt atctaaagtt    1260 tgcaaccta acgtaagtct tgtcagtgtt gtcaccgatc ttgtagtact tttggccgtt    1320
cttgaatgtg tatgaagcac cgtaagtagt tacaacttca ccttcttca atacaacctt    1380 gttagcacgc ttctttgatg atgcgtaaac gtaagcgttg tgcttcaaag tacgcttagt    1440
accatcgatg tttgcagcgt tgatgtactt gtcaacagcc ttaccgtttt caactacttg    1500
gtagtaagtc ttaccgttga tagtagtagt gtttggcaat acgcttactg agttgtaacg    1560
cttaacgctg tcagtaccaa cacgcttagc gtccttgtcg tagtagtatg cgttgtgcat    1620
aattctcttg cttacgctgg ctacagttgg ctcagcaaca ttaggaacag taacaactac    1680
tggcaaagta gctgacttac cattagtatt tgatgctaaa tctgtatcat ctttagtcac    1740
aaacccactt acggcaactg cactcggtgt actaccacca gttacatcaa ctttaagggt    1800
tttgttgaaa tcaatagttg ttcctttgcc tgcatattct aaacctgttg atggaagatt    1860
gattgcaata ccagctgtag aatcacctac tttaccatac ttatcttcaa cagcaccgc    1920 tttcatttcg acaacatatc cggtatcttc actacctcca ctctttaagc caaaagttgc    1980
cacatctttt acttttaacg cttttgttgc cgcaacattc tttccttcag aatcctgcgt    2040
tttagacacc attccaaacg tatctttagt tgcaatatca attagcgtct tttcatttaa    2100
cgaattcaat ttagtaacaa tagcttcggc atcggcttga ttggtgataa tcttattctc    2160
tagattgtaa tcaacagaaa aatctacata atcgccatcg cctaatttgt ctaattgtgt    2220
atttacaaga ttatacaact tttctgcggc tgcatctcga tctgctttct tattcgctga    2280
tttaggtgct acttctccta ccacaccatc attgaaactg accgtaatct taccaatact    2340 attatctttta agtccatctt gtaattgttt gacagccttt ttccaatcat tcttaaccac    2400
cgtatagcct tgtgtaccag tggttgcagc aaatacaggt gcagcagcgc taacagtaga    2460
```

| | | | |
|---|---|---|---|
| tacagcagaa gcagcaactg gagcaacagc aagtaaagca gcagcagcag cgctaacgat | | | 2520 |
| tcttaaattt ttcttcataa tatctccttt taaattcaat gtttcatcca tattttacac | | | 2580 |
| atttcacagt ttttttcata gagatatggg caaaaaaaca tcttttttta tttctacttt | | | 2640 |
| ttattttctg cttttttgtg ctaacttata acaaaagcat actaagagaa gtgtaaaact | | | 2700 |
| attagatttc ttttttcctcc gatcatatga tcggaggaaa aagaagtcta atagatcttc | | | 2760 |
| aatttgatca ataaagctac catctcgctt ttgccaatgg cgccattgtg caccataaac | | | 2820 |
| gtcgcctaaa ttaccatatt ttttggcgaa gttctcatca tcaaggatac gtcgatcaaa | | | 2880 |
| tttttttaat tcagcttgat aaattttatt aaattccgga tcactttgac ttcgtaaacc | | | 2940 |
| aaaatcagtc atatcaggac cagtatattc atcactgtta acccaatttt taaatgccca | | | 3000 |
| ctcatcccaa atatgatttt tatgttctaa taaaaaacga atattagtgt cccctcgtaa | | | 3060 |
| gaaccatagg agttcacttt taattaaacc gaatggaacc ttttttagtgg ttaaaattgg | | | 3120 |
| aaacccttttt gataagtcaa agcgcatttg agcaccaagg ccggcc | | | 3166 |

<210> SEQ ID NO 23
<211> LENGTH: 3667
<212> TYPE: DNA
<213> ORGANISM: Artificial Sequence
<220> FEATURE:
<223> OTHER INFORMATION: Polynucleotide for Lactobacillus integration

<400> SEQUENCE: 23

| | | | |
|---|---|---|---|
| ggccggcccg ggcttgtcag gggactcatt aatgcggccc gtggtatgat caattaaatc | | | 60 |
| attgatggca aaaatgttta tccaacgact tggagatttt tcaacgatca aggggggagtt | | | 120 |
| tcatatgacc gaattttttat gggcacagga tcgcaatggc attatcggca aggatggcca | | | 180 |
| cttgccttgg catctgccag acgatttgca ttattttcgg gcacaaacgg tgggcaaaat | | | 240 |
| catggttgtg gtcggcgta cctacgaaag ctttcctaag cggccgctgc ctgagcgcac | | | 300 |
| gaatgttgtc ttgacccatc aagccgatta tcaggcgccg ggggctgtgg tgctgcatga | | | 360 |
| tgtccccgag gtcttcgctt acgccaagca gcaccctgac caagatctcg ttatcgcagg | | | 420 |
| cggcgcacaa atctttacag ccttttaaaga tgacgttaga tctattagac ttctttttcc | | | 480 |
| tccgatcata tgatcggagg aaaaagaaat ctaatagttt tacacttctc ttagtatgct | | | 540 |
| tttgttataa gttagcacaa aaaagcagaa aataaaaagt agaaataaaa aaagatgtttt | | | 600 |
| ttttgcccat atctctatga aaaaactgt gaaatgtgta aaatatggat gaaacattga | | | 660 |
| atttaaaagg agatattatg aagaaaatt taagaatcgt tagcgctgct gctgctgctt | | | 720 |
| tacttgctgt tgctccagtt gctgcttctg ctgtatctac tgttagcgct gctgcacctg | | | 780 |
| tatttgctgc aaccactggt acacaaggct atacggtggt taagaatgat tggaaaaagg | | | 840 |
| ctgtcaaaca attacaagat ggacttaaag ataatagtat tggtaagatt acggtcagtt | | | 900 |
| tcaatgatgt tgtggtagga gaagtagcac ctaaatcagc gaataagaaa gcagatcgag | | | 960 |
| atgcagccgc agaaaagttg tataatcttg taaatacaca attagacaaa ttaggcgatg | | | 1020 |
| gcgattatgt agatttttct gttgattaca atctagagaa taagattatc accaatcaag | | | 1080 |
| ccgatgccga agctattgtt actaaattga attcgttaaa tgaaagacg ctaattgata | | | 1140 |
| ttgcaactaa agatacgttt ggaatggtgt ctaaaacgca ggattctgaa ggaaagaatg | | | 1200 |
| ttgcggcaac aaaagcgtta aaagtaaaag atgtggcaac ttttggctta aagagtggag | | | 1260 |
| gtagtgaaga taccggatat gttgtcgaaa tgaaagcggg tgctgttgaa gataagtatg | | | 1320 |

```
gtaaagtagg tgattctaca gctggtattg caatcaatct tccatcaaca ggtttagaat    1380
atgcaggcaa aggaacaact attgatttca acaaaaccct taaagttgat gtaactggtg    1440
gtagtacacc gagtgcagtt gccgtaagtg ggtttgtgac taaagatgat acagatttag    1500
catcaaatac taatggtaag tcagctactt tgccagtagt tgttactgtt cctaatgttg    1560
ctgagccaac tgtagccagc gtaagcaaga gaattatgca caacgcatac tactacgaca    1620
aggacgctaa gcgtgttggt actgacagcg ttaagcgtta caactcagta agcgtattgc    1680
caaacactac tactatcaac ggtaagactt actaccaagt agttgaaaac ggtaaggctg    1740
ttgacaagta catcaacgct gcaaacatcg atggtactaa gcgtactttg aagcacaacg    1800
cttacgttta cgcatcatca agaagcgtg ctaacaaggt tgtattgaag aagggtgaag    1860
ttgtaactac ttacggtgct tcatacacat tcaagaacgg ccaaaagtac tacaagatcg    1920
gtgacaacac tgacaagact tacgttaagg ttgcaaactt tagataataa gatcttatta    1980
agattaccgt tatccgtgaa aaacgagtgg tagcaattgc taaataacaa aaagagtatg    2040 agttttgct catactcttt ttgttatttg tgcaaatacc gctctacttg tataattaga    2100
acaagtatat aaggaaagta gccgaatatg tttaaaatta ttgttgaatt attcttatta    2160
gtaattattt cagctgctca attacgccat ttattagagt gaggacaagc cctaatgaca    2220
aacaacaaac tgcacttgct tgaatcagaa catgtgttgt gctacggtta ctgtagaatt    2280 cattttaaa aaggggaata tcaggctttc gcatagcaag ctgacggcct aaggggatt    2340 tatatggcta gttttcaatc atttgggata ccaggacagc tggaagtcat caaaaaagca    2400
cttgatcacg tgcgagtcgg tgtggtaatt acagatcccg cacttgaaga taatcctatt    2460
gtctacgtaa atcaaggctt tgttcaaatg accggctacg agaccgagga aattttagga    2520
aagaacgcac gcttcttaca ggaaattta ggaaagaacg cacgcttctt acaggggaaa    2580
cacacagatc ctgcagaagt ggacaacatc agaaccgctt tacaaaataa agaaccggtc    2640
accgttcaga tccaaaacta caaaaaagac ggaacgatgt tctggaatga attaaatatt    2700
gatccaatgg aaatagagga taaaacgtat tttgtcggaa ttcagaatga tatcaccaag    2760
caaaaagaat atgaaaagct tctcgaggat tccctcacgg aaattactgc actttcaact    2820
cctattgtcc cgattcgcaa tggcatttcg gctcttccgc tagtcggaaa cctgacagag    2880
gagcgattta attccatcgt ttgcacattg acgaatatct tatcaacatc caaagatgat    2940
tatttgatca ttgatttatc cggattggcc caagtgaacg aacaaacggc cgaccaaatt    3000
ttcaagctga gccatttgct gaaattgacc ggaactgagt taatcattac tggcattaag    3060
cctgaattgg ctatgaaaat gaataaactg gatgccaatt tttcgtcgct gaaaacatat    3120
tcaaatgtaa aggatgccgt taagtgcttc ccgattatgt aaaaagatcc cgctcaccca    3180
gctggatctt tcagatatct cattttcccg gcaccgtgat caccgtatcg catgatcgct    3240
attttcttga taaagtggcc gatcagctgc tgatcttcaa tggcaacggc cagattgacc    3300
gcgctgtggg tgaattttcc gattacctgg ctaagcaagc cgcgcaaccg acgacgccaa    3360
aagctaagcc tgtcgcaacc aaaccggcac cggaaaaagt tgcgccgaaa gcgaagtcga    3420
aactcacata cgctgaaaaa atagagtatg ataaactgca acaagaactc gatgaactcg    3480
acgagcgctt ggccaaagta aaggcggaaa tggccgatgt caacggcgaa gattacgtta    3540
agttaggtga tcttcaggca agattgacaa aaatcaacca gacgattgac aaaaaattcg    3600
accggttcgc cgagctggat caatatgtat gagcaataaa cgatagaagg ggaaagacgg    3660
tttaaac                                                              3667
```

<210> SEQ ID NO 24
<211> LENGTH: 3667
<212> TYPE: DNA
<213> ORGANISM: Artificial Sequence
<220> FEATURE:
<223> OTHER INFORMATION: Polynucleotide for Lactobacillus integration

<400> SEQUENCE: 24

| | | | | | |
|---|---|---|---|---|---|
| gtttaaaccg | tctttcccct | tctatcgttt | attgctcata | catattgatc | cagctcggcg | 60 |
| aaccggtcga | attttttgtc | aatcgtctgg | ttgattttgt | caatctttgc | ctgaagatca | 120 |
| cctaacttaa | cgtaatcttc | gccgttgaca | tcggccattt | ccgcctttac | tttggccaag | 180 |
| cgctcgtcga | gttcatcgag | ttcttgttgc | agtttatcat | actctatttt | ttcagcgtat | 240 |
| gtgagtttcg | acttcgcttt | cggcgcaact | ttttccggtg | ccggtttggt | tgcgacaggc | 300 |
| ttagcttttg | gcgtcgtcgg | ttgcgcggct | tgcttagcca | ggtaatcgga | aaattcaccc | 360 |
| acagcgcggt | caatctggcc | gttgccattg | aagatcagca | gctgatcggc | cactttatca | 420 |
| agaaaatagc | gatcatgcga | tacggtgatc | acggtgccgg | aaaatgaga | tatctgaaag | 480 |
| atccagctgg | gtgagcggga | tcttttttaca | taatcggaag | cactttaacg | gcatccttta | 540 |
| catttgaata | tgttttcagc | gacgaaaaat | tggcatccag | tttattcatt | ttcatagcca | 600 |
| attcaggctt | aatgccagta | atgattaact | cagttccggt | caatttcagc | aaatggctca | 660 |
| gcttgaaaat | ttggtcggcc | gtttgttcgt | tcacttgggc | caatccggat | aaatcaatga | 720 |
| tcaaataatc | atctttggat | gttgataaga | tattcgtcaa | tgtgcaaacg | atggaattaa | 780 |
| atcgctcctc | tgtcaggttt | ccgactagcg | gaagagccga | aatgccattg | cgaatcggga | 840 |
| caataggagt | tgaaagtgca | gtaatttccg | tgagggaatc | ctcgagaagc | ttttcatatt | 900 |
| cttttttgctt | ggtgatatca | ttctgaattc | cgacaaaata | cgttttatcc | tctatttcca | 960 |
| ttggatcaat | atttaattca | ttccagaaca | tcgttccgtc | ttttttgtag | ttttggatct | 1020 |
| gaacggtgac | cggttcttta | ttttgtaaag | cggttctgat | gttgtccact | tctgcaggat | 1080 |
| ctgtgtgttt | cccctgtaag | aagcgtgcgt | tctttcctaa | aatttcctgt | aagaagcgtg | 1140 |
| cgttctttcc | taaaatttcc | tcggtctcgt | agccggtcat | ttgaacaaag | ccttgattta | 1200 |
| cgtagacaat | aggattatct | tcaagtgcgg | gatctgtaat | taccacaccg | actcgcacgt | 1260 |
| gatcaagtgc | ttttttgatg | acttccagct | gtcctggtat | cccaaatgat | tgaaaactag | 1320 |
| ccatataaat | ccccccttagg | ccgtcagctt | gctatgcgaa | agcctgatat | tcccctttt | 1380 |
| aaaaatgaat | tctacagtaa | ccgtagcaca | acacatgttc | tgattcaagc | aagtgcagtt | 1440 |
| tgttgtttgt | cattagggct | tgtcctcact | ctaataaatg | gcgtaattga | gcagctgaaa | 1500 |
| taattactaa | taagaataat | tcaacaataa | ttttaaacat | attcggctac | tttccttata | 1560 |
| tacttgttct | aattatacaa | gtagagcggt | atttgcacaa | ataacaaaaa | gagtatgagc | 1620 |
| aaaaactcat | actcttttg | ttatttagca | attgctacca | ctcgttttc | acggataacg | 1680 |
| gtaatcttaa | taagatctta | ttatctaaag | tttgcaacct | taacgtaagt | cttgtcagtg | 1740 |
| ttgtcaccga | tcttgtagta | cttttggccg | ttcttgaatg | tgtatgaagc | accgtaagta | 1800 |
| gttacaactt | cacccttctt | caatacaacc | ttgttagcac | gcttctttga | tgatgcgtaa | 1860 |
| acgtaagcgt | tgtgcttcaa | agtacgctta | gtaccatcga | tgtttgcagc | gttgatgtac | 1920 |
| ttgtcaacag | ccttaccgtt | tcaactact | tggtagtaag | tcttaccgtt | gatagtagta | 1980 |
| gtgtttggca | atacgcttac | tgagttgtaa | cgcttaacgc | tgtcagtacc | aacacgctta | 2040 |

```
gcgtccttgt cgtagtagta tgcgttgtgc ataattctct tgcttacgct ggctacagtt    2100
ggctcagcaa cattaggaac agtaacaact actggcaaag tagctgactt accattagta    2160
tttgatgcta aatctgtatc atctttagtc acaaacccac ttacggcaac tgcactcggt    2220
gtactaccac cagttacatc aactttaagg gttttgttga aatcaatagt tgttcctttg    2280
cctgcatatt ctaaacctgt tgatggaaga ttgattgcaa taccagctgt agaatcacct    2340
actttaccat acttatcttc aacagcaccc gctttcattt cgacaacata tccggtatct    2400
tcactacctc cactctttaa gccaaaagtt gccacatctt ttactttaa cgcttttgtt     2460 gccgcaacat tctttccttc agaatcctgc gttttagaca ccattccaaa cgtatcttta    2520
gttgcaatat caattagcgt cttttcattt aacgaattca atttagtaac aatagcttcg    2580
gcatcggctt gattggtgat aatcttattc tctagattgt aatcaacaga aaatctaca    2640 taatcgccat cgcctaattt gtctaattgt gtatttacaa gattatacaa cttttctgcg    2700
gctgcatctc gatctgcttt cttattcgct gatttaggtg ctacttctcc taccacacca    2760
tcattgaaac tgaccgtaat cttaccaata ctattatctt taagtccatc ttgtaattgt    2820
ttgacagcct ttttccaatc attcttaacc accgtatagc cttgtgtacc agtggttgca    2880
gcaaatacag gtgcagcagc gctaacagta gatacagcag aagcagcaac tggagcaaca    2940
gcaagtaaag cagcagcagc agcgctaacg attcttaaat ttttcttcat aatatctcct    3000
tttaaattca atgtttcatc catattttac acatttcaca gtttttttca tagagatatg    3060
ggcaaaaaaa catctttttt tatttctact tttatttttc tgcttttttg tgctaactta    3120
taacaaaagc atactaagag aagtgtaaaa ctattagatt tctttttcct ccgatcatat    3180
gatcggagga aaaagaagtc taatagatct aacgtcatct ttaaaggctg taaagatttg    3240
tgcgccgcct gcgataacga gatcttggtc agggtgctgc ttggcgtaag cgaagacctc    3300
ggggacatca tgcagcacca cagcccccgg cgcctgataa tcggcttgat gggtcaagac    3360
aacattcgtg cgctcaggca gcggccgctt aggaaagctt tcgtaggtac gccgaccac    3420 aaccatgatt ttgcccaccg tttgtgcccg aaaataatgc aaatcgtctg gcagatgcca    3480
aggcaagtgg ccatccttgc cgataatgcc attgcgatcc tgtgcccata aaaattcggt    3540
catatgaaac tccccttga tcgttgaaaa atctccaagt cgttggataa acattttgc     3600 catcaatgat ttaattgatc ataccacggg ccgcattaat gagtcccctg acaagcccgg    3660
gccggcc                                                             3667

<210> SEQ ID NO 25
<211> LENGTH: 3166
<212> TYPE: DNA
<213> ORGANISM: Artificial Sequence
<220> FEATURE:
<223> OTHER INFORMATION: Polynucleotide for Lactobacillus integration

<400> SEQUENCE: 25
ggccggcctt ggtgctcaaa tgcgctttga cttatcaaaa gggtttccaa ttttaaccac       60
taaaaaggtt ccattcggtt taattaaaag tgaactccta tggttcttac gagggggacac    120 taatattcgt tttttattag aacataaaaa tcatatttgg gatgagtggg catttaaaaa    180
ttgggttaac agtgatgaat atactggtcc tgatatgact gattttggtt tacgaagtca    240
aagtgatccg gaatttaata aaatttatca agctgaatta aaaaaatttg atcgacgtat    300
ccttgatgat gagaacttcg ccaaaaaata tggtaattta ggcgacgttt atggtgcaca    360
atggcgccat tggcaaaagc gagatggtag ctttattgat caaattgaag atcgattaga    420
```

```
cttctttttc ctccgatcat atgatcggag gaaaaagaaa tctaatagtt ttacacttct      480
cttagtatgc ttttgttata agttagcaca aaaaagcaga aaataaaaag tagaaataaa      540
aaaagatgtt tttttgccca tatctctatg aaaaaaactg tgaaatgtgt aaaatatgga      600
tgaaacattg aatttaaaag gagatattat gaagaaaaat ttaagaatcg ttagcgctgc      660
tgctgctgct ttacttgctg ttgctccagt tgctgcttct gctgtatcta ctgttagcgc      720
tgctgcacct gtatttgctg caaccactgg tacacaaggc tatacggtgg ttaagaatga      780
ttggaaaaag gctgtcaaac aattacaaga tggacttaaa gataatagta ttggtaagat      840
tacggtcagt ttcaatgatg gtgtggtagg agaagtagca cctaaatcag cgaataagaa      900
agcagatcga gatgcagccg cagaaaagtt gtataatctt gtaaatacac aattagacaa      960
attaggcgat ggcgattatg tagatttttc tgttgattac aatctagaga ataagattat     1020
caccaatcaa gccgatgccg aagctattgt tactaaattg aattcgttaa atgaaaagac     1080
gctaattgat attgcaacta agatacgtt tggaatggtg tctaaaacgc aggattctga     1140
aggaaagaat gttgcggcaa caaaagcgtt aaaagtaaaa gatgtggcaa cttttggctt     1200
aaagagtgga ggtagtgaag ataccggata tgttgtcgaa atgaaagcgg gtgctgttga     1260
agataagtat ggtaaagtag gtgattctac agctggtatt gcaatcaatc ttccatcaac     1320
aggtttagaa tatgcaggca aaggaacaac tattgatttc aacaaaaccc ttaaagttga     1380
tgtaactggt ggtagtacac cgagtgcagt tgccgtaagt gggtttgtga ctaaagatga     1440
tacagattta gcatcaaata ctaatggtaa gtcagctact ttgccagtag ttgttactgt     1500
tcctaatgtt gctgagccaa ctgtagccag cgtaagcaag agaattatgc acaacgcata     1560
ctactacgac aaggacgcta agcgtgttgg tactgacagc gttaagcgtt acaactcagt     1620
aagcgtattg ccaaacacta ctactatcaa cggtaagact tactaccaag tagttgaaaa     1680
cggtaaggct gttgacaagt acatcaacgc tgcaaacatc gatggtacta agcgtacttt     1740
gaagcacaac gcttacgttt acgcatcatc aaagaagcgt gctaacaagg ttgtattgaa     1800
gaagggtgaa gttgtaacta cttacggtgc ttcatacaca ttcaagaacg gccaaaagta     1860
ctacaagatc ggtgacaaca ctgacaagac ttacgttaag gttgcaaact ttagataata     1920
agatcttatt aagattaccg ttatccgtga aaaacgagtg gtagcaattg ctaaataaca     1980
aaaagagtat gagttttttgc tcatactctt tttgttattt gtgcaaatac cgctctactt     2040
gtataattag aacaagtata taaggaaagt agccgaatat gtttaaaatt attgttgaat     2100
tattcttatt agtaattatt tcagctgctc aattacgcca tttattagag ggcgcgcctg     2160
aggacaagcc ctaatgacaa acaacaaact gcacttgctt gaatcagaac atgtgttgtg     2220
ctacggttac tgtagaattc attttttaaaa aggggaatat caggctttcg catagcaagc     2280
tgacggccta aggggggattt atatggctag ttttcaatca tttgggatac caggacagct     2340
ggaagtcatc aaaaaagcac ttgatcacgt gcgagtcggt gtggtaatta cagatcccgc     2400
acttgaagat aatcctattg tctacgtaaa tcaaggcttt gttcaaatga ccggctacga     2460
gaccgaggaa attttaggaa agaacgcacg cttcttacag gaaattttag gaaagaacgc     2520
acgcttctta caggggaaac acacagatcc tgcagaagtg gacaacatca gaaccgcttt     2580
acaaaataaa gaaccggtca ccgttcagat ccaaaactac aaaaaagacg gaacgatgtt     2640
ctggaatgaa ttaaatattg atccaatgga aatagaggat aaaacgtatt ttgtcggaat     2700
tcagaatgat atcaccaagc aaaaagaata tgaaaagctt ctcgaggatt ccctcacgga     2760
```

| | |
|---|---|
| aattactgca ctttcaactc ctattgtccc gattcgcaat ggcatttcgg ctcttccgct | 2820 |
| agtcggaaac ctgacagagg agcgatttaa ttccatcgtt tgcacattga cgaatatctt | 2880 |
| atcaacatcc aaagatgatt atttgatcat tgatttatcc ggattggccc aagtgaacga | 2940 |
| acaaacggcc gaccaaattt tcaagctgag ccatttgctg aaattgaccg gaactgagtt | 3000 |
| aatcattact ggcattaagc ctgaattggc tatgaaaatg aataaactgg atgccaattt | 3060 |
| ttcgtcgctg aaaacatatt caaatgtaaa ggatgccgtt aaagtgcttc cgattatgta | 3120 |
| aaaagatccc gctcacccag ctggatcttt cagatatcgt ttaaac | 3166 |

<210> SEQ ID NO 26
<211> LENGTH: 3166
<212> TYPE: DNA
<213> ORGANISM: Artificial Sequence
<220> FEATURE:
<223> OTHER INFORMATION: Polynucleotide for Lactobacillus integration

<400> SEQUENCE: 26

| | |
|---|---|
| gtttaaacga tatctgaaag atccagctgg gtgagcggga tcttttttaca taatcggaag | 60 |
| cactttaacg gcatccttta catttgaata tgttttcagc gacgaaaaat tggcatccag | 120 |
| tttattcatt ttcatagcca attcaggctt aatgccagta atgattaact cagttccggt | 180 |
| caatttcagc aaatggctca gcttgaaaat ttggtcggcc gtttgttcgt tcacttgggc | 240 |
| caatccggat aaatcaatga tcaaataatc atctttggat gttgataaga tattcgtcaa | 300 |
| tgtgcaaacg atggaattaa atcgctcctc tgtcaggttt ccgactagcg aagagccga | 360 |
| aatgccattg cgaatcggga cataggagt tgaaagtgca gtaatttccg tgagggaatc | 420 |
| ctcgagaagc ttttcatatt ctttttgctt ggtgatatca ttctgaattc cgacaaaata | 480 |
| cgttttatcc tctatttcca ttggatcaat atttaattca ttccagaaca tcgttccgtc | 540 |
| ttttttgtag ttttggatct gaacggtgac cggttcttta ttttgtaaag cggttctgat | 600 |
| gttgtccact tctgcaggat ctgtgtgttt ccctgtaag aagcgtgcgt tctttcctaa | 660 |
| aatttcctgt aagaagcgtg cgttctttcc taaaatttcc tcggtctcgt agccggtcat | 720 |
| ttgaacaaag ccttgattta cgtagacaat aggattatct tcaagtgcgg gatctgtaat | 780 |
| taccacaccg actcgcacgt gatcaagtgc ttttttgatg acttccagct gtcctggtat | 840 |
| cccaaatgat tgaaaactag ccatataaat cccccttagg ccgtcagctt gctatgcgaa | 900 |
| agcctgatat tcccctttt aaaaatgaat tctacagtaa ccgtagcaca acacatgttc | 960 |
| tgattcaagc aagtgcagtt tgttgtttgt cattagggct tgtcctcagg cgcgccctct | 1020 |
| aataaatggc gtaattgagc agctgaaata attactaata agaataattc aacaataatt | 1080 |
| ttaaacatat tcggctactt tccttatata cttgttctaa ttatacaagt agagcggtat | 1140 |
| ttgcacaaat aacaaaaaga gtatgagcaa aaactcatac tcttttttgtt atttagcaat | 1200 |
| tgctaccact cgttttttcac ggataacggt aatcttaata agatcttatt atctaaagtt | 1260 |
| tgcaacctta acgtaagtct tgtcagtgtt gtcaccgatc ttgtagtact tttggccgtt | 1320 |
| cttgaatgtg tatgaagcac cgtaagtagt tacaacttca cccttcttca atacaacctt | 1380 |
| gttagcacgc ttctttgatg atgcgtaaac gtaagcgttg tgcttcaaag tacgcttagt | 1440 |
| accatcgatg tttgcagcgt tgatgtactt gtcaacagcc ttaccgtttt caactacttg | 1500 |
| gtagtaagtc ttaccgttga tagtagtagt gtttggcaat acgcttactg agttgtaacg | 1560 |
| cttaacgctc tcagtaccaa cacgcttagc gtccttgtcg tagtagtatg cgttgtgcat | 1620 |
| aattctcttg cttacgctgg ctacagttgg ctcagcaaca ttaggaacag taacaactac | 1680 |

```
tggcaaagta gctgacttac cattagtatt tgatgctaaa tctgtatcat ctttagtcac    1740
aaacccactt acggcaactg cactcggtgt actaccacca gttacatcaa ctttaagggt    1800
tttgttgaaa tcaatagttg ttcctttgcc tgcatattct aaacctgttg atggaagatt    1860
gattgcaata ccagctgtag aatcacctac tttaccatac ttatcttcaa cagcacccgc    1920
tttcatttcg acaacatatc cggtatcttc actacctcca ctctttaagc caaaagttgc    1980
cacatctttt acttttaacg cttttgttgc cgcaacattc tttccttcag aatcctgcgt    2040
tttagacacc attccaaacg tatctttagt tgcaatatca attagcgtct tttcatttaa    2100
cgaattcaat ttagtaacaa tagcttcggc atcggcttga ttggtgataa tcttattctc    2160
tagattgtaa tcaacagaaa atctacata atcgccatcg cctaatttgt ctaattgtgt    2220
atttacaaga ttatacaact tttctgcggc tgcatctcga tctgctttct tattcgctga    2280
tttaggtgct acttctccta ccacaccatc attgaaactg accgtaatct taccaatact    2340
attatcttta agtccatctt gtaattgttt gacagccttt ttccaatcat tcttaaccac    2400
cgtatagcct tgtgtaccag tggttgcagc aaatacaggt gcagcagcgc taacagtaga    2460
tacagcagaa gcagcaactg gagcaacagc aagtaaagca gcagcagcag cgctaacgat    2520
tcttaaattt ttcttcataa tatctccttt taaattcaat gtttcatcca tattttacac    2580
atttcacagt ttttttcata gagatatggg caaaaaaaca tctttttta tttctacttt    2640 ttattttctg cttttttgtg ctaacttata acaaaagcat actaagagaa gtgtaaaact    2700
attagatttc tttttcctcc gatcatatga tcggaggaaa aagaagtcta atagatcttc    2760
aatttgatca ataaagctac catctcgctt ttgccaatgg cgccattgtg caccataaac    2820
gtcgcctaaa ttaccatatt ttttggcgaa gttctcatca tcaaggatac gtcgatcaaa    2880 ttttttttaat tcagcttgat aaattttatt aaattccgga tcactttgac ttcgtaaacc    2940
aaaatcagtc atatcaggac cagtatattc atcactgtta acccaatttt taaatgccca    3000
ctcatcccaa atatgatttt tatgttctaa taaaaaacga atattagtgt ccctcgtaa    3060 gaaccatagg agttcacttt taattaaacc gaatggaacc ttttagtgg ttaaaattgg    3120 aaacccttt gataagtcaa agcgcatttg agcaccaagg ccggcc                   3166
```

<210> SEQ ID NO 27
<211> LENGTH: 3720
<212> TYPE: DNA
<213> ORGANISM: Artificial Sequence
<220> FEATURE:
<223> OTHER INFORMATION: Polynucleotide for Lactobacillus integration

<400> SEQUENCE: 27

```
ggccggccgg tgaagtaatg attgaatatg tttgggcaga agataaagaa aaaaatattg      60
gcttgaatgg acatttacca tggtatttgc cggctgatat gaagcatttt aaagaagtaa     120
caattaatca tccaataatt atgggaagaa aaacatttga agttttcct aatttgttac     180 ctaaaagaaa acatattgtt ttaactcata tgaagagct aaaaaataaa tatcaaaata     240
atgatcaagt gactatttta cccacagttg aagatttaca taattttgtg gcagaacatc     300
aagatgagcg gatgtgtgca attggtggag tgtcgatttt taacgcttta atggaccaag     360
tagaagtatt agaaaaaacg gagatagatg cgattttga agcagatact aaaatgcctg     420
aaattgatta tagccgtttt aatttagtag cagatcatta gacttctttt tcctccgatc     480
atatgatcgg aggaaaaaga atctaatag ttttacactt ctcttagtat gcttttgtta     540
```

```
taagttagca caaaaaagca gaaaataaaa agtagaaata aaaaaagatg ttttttttgcc    600
catatctcta tgaaaaaaac tgtgaaatgt gtaaaatatg gatgaaacat tgaatttaaa    660
aggagatatt atgaagaaaa atttaagaat cgttagcgct gctgctgctg ctttacttgc    720
tgttgctcca gttgctgctt ctgctgtatc tactgttagc gctgctgcac ctgtatttgc    780
tgcaaccact ggtacacaag gctatacggt ggttaagaat gattggaaaa aggctgtcaa    840
acaattacaa gatggactta agataatag tattggtaag attacggtca gtttcaatga     900
tggtgtggta ggagaagtag cacctaaatc agcgaataag aaagcagatc gagatgcagc    960
cgcagaaaag ttgtataatc ttgtaaatac acaattagac aaattaggcg atggcgatta   1020
tgtagatttt tctgttgatt acaatctaga gaataagatt atcaccaatc aagccgatgc   1080
cgaagctatt gttactaaat tgaattcgtt aaatgaaaag acgctaattg atattgcaac   1140
taaagatacg tttggaatgg tgtctaaaac gcaggattct gaaggaaaga atgttgcggc   1200
aacaaaagcg ttaaaagtaa aagatgtggc aacttttggc ttaaagagtg gaggtagtga   1260
agataccgga tatgttgtcg aaatgaaagc gggtgctgtt gaagataagt atggtaaagt   1320
aggtgattct acagctggta ttgcaatcaa tcttccatca acaggtttag aatatgcagg   1380
caaaggaaca actattgatt tcaacaaaac ccttaaagtt gatgtaactg gtggtagtac   1440
accgagtgca gttgccgtaa gtgggtttgt gactaaagat gatacagatt tagcatcaaa   1500
tactaatggt aagtcagcta cttttgccagt agttgttact gttcctaatg ttgctgagcc   1560
aactgtagcc agcgtaagca agagaattat gcacaacgca tactactacg acaaggacgc   1620
taagcgtgtt ggtactgaca gcgttaagcg ttacaactca gtaagcgtat tgccaaacac   1680
tactactatc aacggtaaga cttactacca agtagttgaa aacggtaagg ctgttgacaa   1740
gtacatcaac gctgcaaaca tcgatggtac taagcgtact ttgaagcaca acgcttacgt   1800
ttacgcatca tcaaagaagc gtgctaacaa ggttgtattg aagaagggtg aagttgtaac   1860
tacttacggt gcttcataca cattcaagaa cggccaaaag tactacaaga tcggtgacaa   1920
cactgacaag acttacgtta aggttgcaaa ctttagataa taagatctta ttaagattac   1980
cgttatccgt gaaaaacgag tggtagcaat tgctaaataa caaaaagagt atgagttttt   2040
gctcatactc ttttttgttat ttgtgcaaat accgctctac ttgtataatt agaacaagta   2100
tataaggaaa gtagccgaat atgtttaaaa ttattgttga attattctta ttagtaatta   2160
tttcagctgc tcaattacgc catttattag agtgaggaca agccctaatg acaaacaaca   2220
aactgcactt gcttgaatca gaacatgtgt tgtgctacgg ttactgtaga attcattttt   2280
aaaaagggga atatcaggct ttcgcatagc aagctgacgg cctaagggg atttatatgg     2340
ctagttttca atcatttggg ataccaggac agctggaagt catcaaaaaa gcacttgatc   2400
acgtgcgagt cggtgtggta attacagatc ccgcacttga agataatcct attgtctacg   2460
taaatcaagg ctttgttcaa atgaccggct acgagaccga ggaaatttta ggaaagaacg   2520
cacgcttctt acaggaaatt ttaggaaaga acgcacgctt cttacagggg aaacacacag   2580
atcctgcaga agtggacaac atcagaaccg ctttacaaaa taagaaccg gtcaccgttc    2640
agatccaaaa ctacaaaaaa gacgaacga tgttctggaa tgaattaaat attgatccaa     2700
tggaaataga ggataaaacg tattttgtcg gaattcagaa tgatatcacc aagcaaaaag   2760
aatatgaaaa gcttctcgag gattccctca cggaaattac tgcactttca actcctattg   2820
tcccgattcg caatggcatt tcggctcttc cgctagtcgg aaacctgaca gaggagcgat   2880
ttaattccat cgtttgcaca ttgacgaata tcttatcaac atccaaagat gattatttga   2940
```

| | |
|---|---:|
| tcattgattt atccggattg gcccaagtga acgaacaaac ggccgaccaa attttcaagc | 3000 |
| tgagccattt gctgaaattg accggaactg agttaatcat tactggcatt aagcctgaat | 3060 |
| tggctatgaa aatgaataaa ctggatgcca atttttcgtc gctgaaaaca tattcaaatg | 3120 |
| taaaggatgc cgttaaagtg cttccgatta tgtaaaaaga tcccgctcac ccagctggat | 3180 |
| ctttcagata tccctgatcg cgccattatg gggatttctg gtgggatttt tattgggttt | 3240 |
| attttaaata taattgcatc tcaatttaat cattcggcat cagatttatt tgtgattgtc | 3300 |
| ttcagttcat cagttttacc aggaatgatt ccatggtttg taattctatt ggctgagtta | 3360 |
| agatttagaa gacataatca agatatgatg aaagatcacc cgttcaaatt gccgttatat | 3420 |
| ccattttcta attacttcgc atttttaatg ctgttagtaa ttgttatctt tatgtttatt | 3480 |
| aatccagata ctagaatttc agtaattacc ggagcattgg tattaattgt ggctacaatt | 3540 |
| gtttatttag ttagacataa agatgaattt agtaaaaata attaatgatt aagaagtctt | 3600 |
| gaaatttcag ggcttttat ttttaccaaa tactaaatat tgatacttgc attatcaaaa | 3660 |
| atactagatc tatggtatct taaaaagaaa tgatacttaa agggtgagat aagtttaaac | 3720 |

<210> SEQ ID NO 28
<211> LENGTH: 3720
<212> TYPE: DNA
<213> ORGANISM: Artificial Sequence
<220> FEATURE:
<223> OTHER INFORMATION: Polynucleotide for Lactobacillus integration

<400> SEQUENCE: 28

| | |
|---|---:|
| gtttaaactt atctcaccct ttaagtatca tttcttttta agataccata gatctagtat | 60 |
| ttttgataat gcaagtatca atatttagta tttggtaaaa ataaaaagcc ctgaaatttc | 120 |
| aagacttctt aatcattaat tatttttact aaattcatct ttatgtctaa ctaaataaac | 180 |
| aattgtagcc acaattaata ccaatgctcc ggtaattact gaaattctag tatctggatt | 240 |
| aataaacata aagataacaa ttactaacag cattaaaaat gcgaagtaat tagaaaatgg | 300 |
| atataacggc aatttgaacg ggtgatcttt catcatatct tgattatgtc ttctaaatct | 360 |
| taactcagcc aatagaatta caaaccatgg aatcattcct ggtaaaactg atgaactgaa | 420 |
| gacaatcaca aataaatctg atgccgaatg attaaattga gatgcaatta tatttaaaat | 480 |
| aaacccaata aaaatcccac cagaaatccc cataatggcg cgatcaggga tatctgaaag | 540 |
| atccagctgg gtgagcggga tcttttttaca taatcggaag cactttaacg gcatccttta | 600 |
| catttgaata tgttttcagc gacgaaaaat tggcatccag tttattcatt ttcatagcca | 660 |
| attcaggctt aatgccagta atgattaact cagttccggt caatttcagc aaatggctca | 720 |
| gcttgaaaat ttggtcggcc gtttgttcgt tcacttgggc caatccggat aaatcaatga | 780 |
| tcaaataatc atctttggat gttgataaga tattcgtcaa tgtgcaaacg atggaattaa | 840 |
| atcgctcctc tgtcaggttt ccgactagcg gaagagccga aatgccattg cgaatcggga | 900 |
| caataggagt tgaaagtgca gtaatttccg tgagggaatc ctcgagaagc ttttcatatt | 960 |
| ctttttgctt ggtgatatca ttctgaattc cgacaaaata cgttttatcc tctatttcca | 1020 |
| ttggatcaat atttaattca ttccagaaca tcgttccgtc ttttttgtag ttttggatct | 1080 |
| gaacggtgac cggttcttta ttttgtaaag cggttctgat gttgtccact tctgcaggat | 1140 |
| ctgtgtgttt cccctgtaag aagcgtgcgt tcttcctaa aatttcctgt aagaagcgtg | 1200 |
| cgttctttcc taaaatttcc tcggtctcgt agccggtcat ttgaacaaag ccttgattta | 1260 |

```
cgtagacaat aggattatct tcaagtgcgg gatctgtaat taccacaccg actcgcacgt    1320
gatcaagtgc ttttttgatg acttccagct gtcctggtat cccaaatgat tgaaaactag    1380
ccatataaat cccccttagg ccgtcagctt gctatgcgaa agcctgatat tccccttttt    1440
aaaaatgaat tctacagtaa ccgtagcaca acacatgttc tgattcaagc aagtgcagtt    1500
tgttgtttgt cattagggct tgtcctcact ctaataaatg gcgtaattga gcagctgaaa    1560
taattactaa taagaataat tcaacaataa ttttaaacat attcggctac tttccttata    1620
tacttgttct aattatacaa gtagagcggt atttgcacaa ataacaaaaa gagtatgagc    1680
aaaaactcat actctttttg ttatttagca attgctacca ctcgttttc  acggataacg    1740 gtaatcttaa taagatctta ttatctaaag tttgcaacct taacgtaagt cttgtcagtg    1800
ttgtcaccga tcttgtagta cttttggccg ttcttgaatg tgtatgaagc accgtaagta    1860
gttacaactt cacccttctt caatacaacc ttgttagcac gcttctttga tgatgcgtaa    1920
acgtaagcgt tgtgcttcaa agtacgctta gtaccatcga tgtttgcagc gttgatgtac    1980
ttgtcaacag ccttaccgtt ttcaactact tggtagtaag tcttaccgtt gatagtagta    2040
gtgtttggca atacgcttac tgagttgtaa cgcttaacgc tgtcagtacc aacacgctta    2100
gcgtccttgt cgtagtagta tgcgttgtgc ataattctct tgcttacgct ggctacagtt    2160
ggctcagcaa cattaggaac agtaacaact actggcaaag tagctgactt accattagta    2220
tttgatgcta aatctgtatc atctttagtc acaaacccac ttacggcaac tgcactcggt    2280
gtactaccac cagttacatc aactttaagg gttttgttga aatcaatagt tgttcctttg    2340
cctgcatatt ctaaacctgt tgatggaaga ttgattgcaa taccagctgt agaatcacct    2400
actttaccat acttatcttc aacagcaccc gctttcattt cgacaacata tccggtatct    2460
tcactacctc cactctttaa gccaaaagtt gccacatctt ttacttttaa cgcttttgtt    2520
gccgcaacat tctttccttc agaatcctgc gttttagaca ccattccaaa cgtatcttta    2580
gttgcaatat caattagcgt cttttcattt aacgaattca atttagtaac aatagcttcg    2640
gcatcggctt gattggtgat aatcttattc tctagattgt aatcaacaga aaaatctaca    2700
taatcgccat cgcctaattt gtctaattgt gtatttacaa gattatacaa cttttctgcg    2760
gctgcatctc gatctgcttt cttattcgct gatttaggtg ctacttctcc taccacacca    2820
tcattgaaac tgaccgtaat cttaccaata ctattatctt taagtccatc ttgtaattgt    2880
ttgacagcct ttttccaatc attcttaacc accgtatagc cttgtgtacc agtggttgca    2940
gcaaatacag gtgcagcagc gctaacagta gatacagcag aagcagcaac tggagcaaca    3000
gcaagtaaag cagcagcagc agcgctaacg attcttaaat ttttcttcat aatatctcct    3060
tttaaattca atgtttcatc catatttac  acatttcaca gttttttttca tagagatatg    3120 ggcaaaaaaa catctttttt tatttctact ttttattttc tgcttttttg tgctaactta    3180
taacaaaagc atactaagag aagtgtaaaa ctattagatt tctttttcct ccgatcatat    3240
gatcggagga aaaagaagtc taatgatctg ctactaaatt aaaacggcta taatcaattt    3300
caggcatttt agtatctgct tcaaaaatcg catctatctc cgtttttttct aatacttcta    3360 cttggtccat taaagcgtta aaaatcgaca ctccaccaat tgcacacatc cgctcatctt    3420
```

```
gatgttctgc cacaaaatta tgtaaatctt caactgtggg taaaatagtc acttgatcat  3480
tattttgata tttatttttt agctcttcat tatgagttaa aacaatatgt tttcttttag  3540
gtaacaaatt aggaaaactt tcaaatgttt ttcttcccat aattattgga tgattaattg  3600
ttacttcttt aaaatgcttc atatcagccg gcaaatacca tggtaaatgt ccattcaagc  3660 caatatttt ttctttatct tctgcccaaa catattcaat cattacttca ccggccggcc  3720
```

COMPOSITIONS COMPRISING RECOMBINANT PROBIOTIC BACTERIA AND METHODS OF USE THEREOF

CROSS REFERENCE TO RELATED APPLICATIONS

This application is a continuation of U.S. patent application Ser. No. 16/813,131, filed Mar. 9, 2020, which is a continuation of U.S. patent application Ser. No. 15/545,462, filed Jul. 21, 2017, allowed as U.S. Pat. No. 10,583,186, which is a 3.71 National Entry Application of International Patent Application No. PCT/US16/14590, filed Jan. 22, 2016, which claims priority to and the benefit of U.S. Provisional Application No. 62/107,224, filed Jan. 23, 2015, which are incorporated herein by reference in their entireties.

STATEMENT OF RIGHTS TO INVENTIONS MADE UNDER FEDERALLY SPONSORED RESEARCH

This invention was made with government support under Grant No. 2101BX001183-05A1 awarded by the Department of Veterans Affairs and Grant No. NA/ARZT-5704130-A50-111 awarded by USDA/NIFA. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 64,000 Byte ASCII (Text) file named "37839-304_ST25.TXT," created on Jan. 21, 2021.

BACKGROUND OF THE INVENTION

*Clostridium difficile* infection (CDI) is a leading cause of antibiotic-associated diarrhea in humans and animals, including agriculturally relevant animals such as calves, foals, and piglets. In the U.S., 400,000 human cases are diagnosed annually, and its treatment and prevention imposes over $3 billion in healthcare-associated costs.

CDI is precipitated when commensal flora are suppressed following antibiotic treatment. The use of antibiotics can suppress the protective normal microbiota causing susceptibility to infection. Exposure to *C. difficile* spores results in colonization of the host gastrointestinal tract. Current treatments include use of antibiotics, which have the potential to alter the bacterial composition of the gut microbiome. Vaccines are being developed for preventing *C. difficile* disease, but do not protect against *C. difficile* colonization.

At present, effective treatments and preventatives for *Clostridium difficile* infection and colonization are lacking. New methods of treatment are urgently required.

SUMMARY OF THE INVENTION

As described below, the present invention features probiotic bacteria (e.g., *Lactoccocus lactis* and *Lactobacillus acidophilus*) expressing the *Clostridium difficile* surface protein SlpA, or fragment or chimera thereof, and its use in treating or preventing *Clostridium difficile* infection and colonization.

In one aspect, the invention provides an isolated polypeptide having a bacterial secretion signal, *C. difficile* SlpA variable domain, and *Lactobacillus* SlpA cell wall binding domain.

In another aspect, the invention provides an isolated nucleic acid molecule encoding a polypeptide having a bacterial secretion signal, *C. difficile* SlpA variable domain, and *Lactobacillus* SlpA cell wall binding domain.

In still another aspect, the invention provides a vector having a nucleic acid sequence encoding a polypeptide having a bacterial secretion signal, *C. difficile* SlpA variable domain, and *Lactobacillus* SlpA cell wall binding domain.

In yet another aspect, the invention provides an isolated cell (e.g., bacterial cell) containing a nucleic acid molecule encoding a polypeptide having a bacterial secretion signal, *C. difficile* SlpA variable domain, and *Lactobacillus* SlpA cell wall binding domain or a vector having a nucleic acid sequence encoding a polypeptide having a bacterial secretion signal, *C. difficile* SlpA variable domain, and *Lactobacillus* SlpA cell wall binding domain.

In one aspect, the invention provides a method of treating or preventing *Clostridium difficile* infection in a subject, the method involving administering one or more *Lactococcus* or *Lactobacillus* bacterial strains expressing a chimeric SlpA polypeptide to the gut of the subject, where the chimeric SlpA polypeptide has a bacterial secretion signal, *C. difficile* SlpA variable domain, and *Lactobacillus* SlpA cell wall binding domain, thereby treating or preventing *Clostridium difficile* infection in the subject.

In another aspect, the invention provides a method of colonizing the gut of a subject with one or more *Lactococcus* or *Lactobacillus* bacterial strains, the method comprising administering one or more *Lactococcus* or *Lactobacillus* bacterial strains expressing a chimeric SlpA polypeptide to the gut of the subject, where the chimeric SlpA polypeptide comprises a bacterial secretion signal, *C. difficile* SlpA variable domain, and *Lactobacillus* SlpA cell wall binding domain, thereby colonizing the gut of a subject with *Lactococcus* or *Lactobacillus*.

In another aspect, the invention provides a composition (e.g., a therapeutic or pharmaceutical composition) containing an effective amount of one or more *Lactoccocus* or *Lactobacillus* bacterial strains expressing a chimeric SlpA polypeptide, where the chimeric SlpA polypeptide has a bacterial secretion signal, *C. difficile* SlpA variable domain, and *Lactobacillus* SlpA cell wall binding domain.

In still another aspect, the invention provides a kit for treating or preventing *Clostridium difficile* infection in a subject, the kit comprising one or more *Lactoccocus* or *Lactobacillus* bacterial strains expressing a chimeric SlpA polypeptide, where the chimeric SlpA polypeptide has a bacterial secretion signal, *C. difficile* SlpA variable domain, and *Lactobacillus* SlpA cell wall binding domain and optionally directions for the use of the kit (e.g., in the methods of any aspect of the invention).

In yet another aspect, the invention provides kit for colonizing the gut of a subject with *Lactoccocus* or *Lactobacillus*, the kit containing one or more *Lactoccocus* or *Lactobacillus* bacterial strains expressing a chimeric SlpA polypeptide, where the chimeric SlpA polypeptide has a bacterial secretion signal, *C. difficile* SlpA variable domain, and *Lactobacillus* SlpA cell wall binding domain and optionally directions for the use of the kit (e.g., in the methods of any aspect of the invention).

In various embodiments of any of the aspects delineated herein, the SlpA variable domain has the amino acid sequence (SEQ ID NO: 1):

AAPVFAATTGTQGYTVVKNDWKKAVKQLQDGLKDNSIGKITVSFNDGVVG

EVAPKSANKKADRDAAAEKLYNLVNTQLDKLGDGDYVDFSVDYNLENKII

TNQADAEAIVTKLNSLNEKTLIDIATKDTFGMVSKTQDSEGKNVAATKAL

KVKDVATFGLKSGGSEDTGYVVEMKAGAVEDKYGKVGDSTAGIAINLPST

GLEYAGKGTTIDFNKTLKVDVTGGSTPSAVAVSGFVTKDDTDLA

In various embodiments of any of the aspects delineated herein, the SlpA cell wall binding domain is a *Lactobacillus acidophilus* or *Lactobacillus casei* SlpA cell wall binding domain. In certain embodiments, the SlpA cell wall binding domain has the amino acid sequence (SEQ ID NO: 2):

SNTNGKSATLPVVVTVPNVAEPTVASVSKRIMHNAYYYDKDAKRVGTDSV

KRYNSVSVLPNTTTINGKTYYQVVENGKAVDKYINAANIDGTKRTLKHNA

YVVYASSKKRANKVVLKKGEVVTTYGASYTFKNGQKYYKIGDNTDKTYVKV

ANFR

In various embodiments of any of the aspects delineated herein, the bacterial secretion signal is a *Lactococcus, Lactobacillus, Lactobacillus acidophilus*, or *Lactobacillus casei* secretion signal. In certain embodiments, the bacterial secretion signal has the amino acid sequence (SEQ ID NO: 3):
MKKNLRIVSAAAAALLAVAPVAASAVSTVSA
In particular embodiments, the isolated polypeptide has the amino acid sequence (SEQ ID NO: 4):

| | |
|---|---|
| MKKNLRIVSAAAAALLAVAPVAASAVSTVSAAAPVFAATTGTQGYTVVKN | 50 |
| DWKKAVKQLQDGLKDNSIGKITVSFNDGVVGEVAPKSANKKADRDAAAEK | 100 |
| LYNLVNTQLDKLGDGDYVDFSVDYNLENKIITNQADAEAIVTKLNSLNEK | 150 |
| TLIDIATKDTFGMVSKTQDSEGKNVAATKALKVKDVATFGLKSGGSEDTG | 200 |
| YVVEMKAGAVEDKYGKVGDSTAGIAINLPSTGLEYAGKGTTIDFNKTLKV | 250 |
| DVTGGSTPSAVAVSGFVTKDDTDLASNTNGKSATLPVVVTVPNVAEPTVA | 300 |
| SVSKRIMHNAYYYDKDAKRVGTDSVKRYNSVSVLPNTTTINGKTYYQVVE | 350 |
| NGKAVDKYINAANIDGTKRTLKHNAYVYASSKKRANKVVLKKGEVVTTYG | 400 |
| ASYTFKNGQKYYKIGDNTDKTYVKVANFR* | |

In various embodiments of any of the aspects delineated herein, the isolated nucleic acid molecule contains a sequence optimized for expression in *Lactococcus, Lactococus lactis, Lactobacillus, Lactobacillus acidophilus*, or *Lactobacillus casei*. In specific embodiments, the isolated nucleic acid has the nucleic acid sequence (SEQ ID NO: 5):

GGATCCATGAAGAAAAATTTAAGAATCGTTAGCGCTGCTGCTGCTGCTTT

ACTTGCTGTTGCTCCAGTTGCTGCTTCTGCTGTATCTACTGTTAGCGCTG

CTGCACCTGTATTTGCTGCAACCACTGGTACACAAGGCTATACGGTGGTT

AAGAATGATTGGAAAAGGCTGTCAAACAATTACAAGATGGACTTAAAGA

TAATAGTATTGGTAAGATTACGGTCAGTTTCAATGATGGTGTGGTAGGAG

AAGTAGCACCTAAATCAGCGAATAAGAAAGCAGATCGAGATGCAGCCGCA

GAAAAGTTGTATAATCTTGTAAATACACAATTAGACAAATTAGGCGATGG

CGATTATGTAGATTTTTCTGTTGATTACAATCTAGAGAATAAGATTATCA

CCAATCAAGCCGATGCCGAAGCTATTGTTACTAAATTGAATTCGTTAAAT

GAAAAGACGCTAATTGATATTGCAACTAAAGATACGTTTGGAATGGTGTC

TAAAACGCAGGATTCTGAAGGAAAGAATGTTGCGGCAACAAAAGCGTTAA

AAGTAAAAGATGTGGCAACTTTTGGCTTAAAGAGTGGAGGTAGTGAAGAT

ACCGGATATGTTGTCGAAATGAAAGCGGGTGCTGTTGAAGATAAGTATGG

TAAAGTAGGTGATTCTACAGCTGGTATTGCAATCAATCTTCCATCAACAG

GTTTAGAATATGCAGGCAAAGGAACAACTATTGATTTCAACAAAACCCTT

AAAGTTGATGTAACTGGTGGTAGTACACCGAGTGCAGTTGCCGTAAGTGG

GTTTGTGACTAAAGATGATACAGATTTAGCATCAAATACTAATGGTAAGT

CAGCTACTTTGCCAGTAGTTGTTACTGTTCCTAATGTTGCTGAGCCAACT

GTAGCCAGCGTAAGCAAGAGAATTATGCACAACGCATACTACTACGACAA

GGACGCTAAGCGTGTTGGTACTGACAGCGTTAAGCGTTACAACTCAGTAA

GCGTATTGCCAAACACTACTACTATCAACGGTAAGACTTACTACCAAGTA

GTTGAAAACGGTAAGGCTGTTGACAAGTACATCAACGCTGCAAACATCGA

TGGTACTAAGCGTACTTTGAAGCACAACGCTTACGTTTACGCATCATCAA

AGAAGCGTGCTAACAAGGTTGTATTGAAGAAGGGTGAAGTTGTAACTACT

TACGGTGCTTCATACACATTCAAGAACGGCCAAAAGTACTACAAGATCGG

TGACAACACTGACAAGACTTACGTTAAGGTTGCAAACTTTAGATAATAAA

GATCTTCGAATTCCCGCGGCCGC

In various embodiments of any of the aspects delineated herein, the vector is a *Lactoccocus, Lactobacillus, Lactobacillus acidophilus*, or *Lactobacillus casei* expression vector. In certain embodiments, the vector has a *Lactococcus* or *Lactobacillus* origin of replication. In specific embodiments, the vector is pMGM10, pMGM11, pTRK848, or pTRK882.

In various embodiments of any of the aspects delineated herein, the vector comprises a first sequence identical to a sequence of a first fragment in a *Lactobacillus* genome, wherein the first fragment is located at the 5' or 3' terminus of thyA gene, or within the thyA gene of *Lactobacillus*. In various embodiments of any of the aspects delineated herein, the vector comprises a second sequence identical to a sequence of a second fragment in a *Lactobacillus* genome, wherein the second fragment is located at the 5' or 3' terminus of a thyA gene. In various embodiments of any of the aspects delineated herein, the vector has a sequence identical to a sequence of a fragment in *Lactobacillus acidophilus*, or *Lactobacillus casei* genome.

In various embodiments of any of the aspects delineated herein, the cell is a *Lactoccocus, Lactoccocus lactis, Lactobacillus, Lactobacillus acidophilus,* or *Lactobacillus casei* cell. In various embodiments of any of the aspects delineated herein, the nucleic acid sequence encoding the chimeric SlpA peptide is integrated into the chromosome of the isolated cell.

In various embodiments of any of the aspects delineated herein, the subject is a human or animal.

In various embodiments of any of the aspects delineated herein, the subject has undergone or is undergoing treatment with one or more antibiotics (e.g., a cephalosporin, metronidazole, fluoroquinolone, such as moxifloxacin or vancomycin and fidaxomycin and the like). In various embodiments of any of the aspects delineated herein, the administration of the *Lactoccocus* or *Lactobacillus* expressing a chimeric SlpA polypeptide is by oral administration.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Surface-Layer Protein A (SlpA)" is meant a polypeptide or fragment thereof having at least about 85% or greater amino acid identity to the amino acid sequence provided at NCBI Accession No. CAJ69681 or WP_011254065 and having bacterial adherence activity. Exemplary SlpA amino acid sequences are provided below (SEQ ID NO: 6):

```
Clostridium difficile SlpA (full length sequence)
  1 mnkkniaiam sgltvlasaa pvfaattgtq gytvvkndwk kavkqlqdgl kdnsigkitv 61 sfndgvvgev apksankkad rdaaaeklyn lvntqldklg dgdyvdfsvd ynlenkiitn 121 qadaeaivtk lnslnektli diatkdtfgm vsktqdsegk nvaatkalkv kdvatfglks 181 ggsedtgyvv emkagavedk ygkvgdstag iainlpstgl eyagkgttid fnktlkvdvt 241 ggstpsavav sgfvtkddtd laksgtinvr vinakeesid idassytsae nlakryvfdp 301 deiseaykai valqndgies nlvqlvngky qvifypegkr letksandti asqdtpakvv 361 ikanklkdlk dyvddlktyn ntysnvvtva gedrietaie lsskyynsdd knaitdkavn 421 divlvgstsi vdglvaspla sektaplllt skdkldssvk seikrvmnlk sdtgintskk 481 vylaggvnsi skdvenelkn mglkvtrlsg edryetslai adeigldndk afvvggtgla 541 damsiapvas qlkdgdatpi vvvdgkakei sddaksflgt sdvdiiggkn svskeieesi 601 dsatgktpdr isgddrqatn aevlkeddyf tdgevvnyfv akdgstkedq lvdalaaapi 661 agrfkespap iilatdtlss dqnvavskav pkdggtnlvq vgkgiassvi nkmkdlldm Lactobacillus acidophilus
  1 mkknlrivsa aaaallavap vaasavstvs aattinasss aintntnaky dvdvtpsvsa 61 vaantanntp aiagnltgti sasyngktyt anlkadtena titaagstta vkpaelaagv 121 aytvtvndvs fnfgsenagk tvtlgsansn vkftgtnsdn qtetnvstlk vkldqngvas 181 ltnvsianvy ainttdnsnv nfydvtsgat vtngavsvna dnqgqvnvan vvaainskyf 241 aaqyadkkln trtantedai kaalkdqkid vnsvgyfkap htftvnvkat sntngksatl 301 pvvvtvpnva eptvasvskr imhnayyydk dakrvgtdsv krynsvsvlp ntttingkty 361 yqvvengkav dkyinaanid gtkrtlkhna yvyasskkra nkvvlkkgev vttygasytf 421 kngqkyykig dntdktyvkv anfr
```

By "SlpA nucleic acid molecule" is meant a polynucleotide encoding SlpA.

By "SlpA variable domain" is meant a polypeptide having 85% identity to the following sequence (SEQ ID NO: 1):

AAPVFAATTGTQGYTVVKNDWKKAVKQLQDGLKDNSIGKITVSFNDGVVG

EVAPKSANKKADRDAAAEKLYNLVNTQLDKLGDGDYVDFSVDYNLENKII

TNQADAEAIVTKLNSLNEKTLIDIATKDTFGMVSKTQDSEGKNVAATKAL

KVKDVATFGLKSGGSEDTGYVVEMKAGAVEDKYGKVGDSTAGIAINLPST

GLEYAGKGTTIDFNKTLKVDVTGGSTPSAVAVSGFVTKDDTDLA

In one embodiment, the SlpA variable domain is from *C. difficile* SlpA.

By "SlpA cell wall binding domain" is meant a polypeptide having 85% identity to the following sequence (SEQ ID NO: 8):

```
agedrietaielsskyynsddknaitdkavndivlvgstsivdglvaspl asektaplllltskdkldssvkseikrvmnlksdtgintskkvylaggvns iskdvenelknmglkvtrlsgedryetslaiadeigldndkafvvggtgl adamsiapvasqlkdgdatpivvvdgkakeisddaksflgtsdvdiiggk nsvskeieesidsatgktpdrisgddrqatnaevlkeddyftdgevvnyf vakdgstkedqlvdalaaapiagrfkespapiilatdtlssdqnvavska vpkdggtnlvqvgkgiassvink
```

In one embodiment, the SlpA cell wall binding domain is from *Lactobacillus* (e.g., *Lactobacillus acidophilus*).

By "chimeric SlpA" is meant a polypeptide having two or more SlpA sequences from two or more bacterial strains. In one embodiment, a chimeric SlpA has an SlpA variable domain from *C. difficile* SlpA and an SlpA cell wall binding from *Lactobacillus acidophilus*. In another embodiment, a chimeric SlpA has an SlpA signal sequence from *Lactobacillus acidophilus*, an SlpA variable domain from *C. difficile* SlpA and an SlpA cell wall binding from *Lactobacillus acidophilus*. An exemplary chimeric SlpA sequence is provided below (SEQ ID NO: 7):

```
MKKNLRIVSAAAAALLAVAPVAASAVSTVSAAAPVFAATTGTQGYTVVKN    50

DWKKAVKQLQDGLKDNSIGKITVSFNDGVVGEVAPKSANKKADRDAAAEK   100

LYNLVNTQLDKLGDGDYVDFSVDYNLENKIITNQADAEAIVTKLNSLNEK   150

TLIDIATKDTFGMVSKTQDSEGKNVAATKALKVKDVATFGLKSGGSEDTG   200

YVVEMKAGAVEDKYGKVGDSTAGIAINLPSTGLEYAGKGTTIDFNKTLKV   250

DVTGGSTPSAVAVSGFVTKDDTDLASNTNGKSATLPVVVTVPNVAEPTVA   300

SVSKRIMHNAYYYDKDAKRVGTDSVKRYNSVSVLPNTTTINGKTYYQVVE   350

NGKAVDKYINAANIDGTKRTLKHNAYVYASSKKRANKVVLKKGEVVTTYG   400

ASYTFKNGQKYYKIGDNTDKTYVKVANFR*
```

A codon-optimized nucleic acid sequence of the above chimeric SlpA sequence for expression in *Lactobacillus* is provided below at FIG. 1C.

By "undesirable gut microbiome" is meant a community of microbes comprising a pathogen or having a biological activity associated with a pathogenic process. In one embodiment, an undesirable gut microbiome comprises an increased number or percentage of *Clostridium difficile* relative to the number or percentage of *C. difficile* present in the gut of a healthy control subject.

By "normal gut flora" is meant a population of microbes that is substantially similar to the population of microbes present in the gut of a healthy control subject.

By "ameliorate" is meant decrease, suppress, attenuate, diminish, arrest, or stabilize the development or progression of a disease.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "effective amount" is meant the amount of a composition of the invention (e.g., comprising a probiotic bacteria expressing *Clostridium difficile* SlpA, or fragment thereof) required to ameliorate the symptoms of a disease relative to an untreated patient. The effective amount of probiotic bacteria of the invention varies depending upon the manner of administration, the age, body weight, and general health of the subject. Ultimately, the attending physician or veterinarian will decide the appropriate amount and dosage regimen. Such amount is referred to as an "effective" amount.

By "expression vector" is meant a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as plasmids, cosmids, and viruses that incorporate the recombinant polynucleotide.

By "fragment" is meant a portion of a polypeptide or nucleic acid molecule. This portion contains, preferably, at least 10%, 20%, 30%, 40%, 50%, 60%, 70%, 80%, or 90% of the entire length of the reference polypeptide or nucleic acid molecule. A fragment may contain 5, 10, 15, 20, 30, 40, 50, 60, 70, 80, 90, or 100 amino acids or nucleotides.

The terms "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. Thus, a purified isolated bacterium that is part of a culture or inoculum is at least about 90%, 95% or 100% free of bacteria, fungi, viruses, or other undefined microbes.

By "marker" is meant any analyte associated with a disease or disorder.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence.

Generally, operably linked DNA sequences are contiguous and, where necessary to join two protein coding regions, in the same reading frame.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

By "reference" is meant a standard or control condition.

A "reference sequence" is a defined sequence used as a basis for sequence comparison.

By "subject" is meant a mammal, including, but not limited to, a human or non-human mammal, such as a bovine, equine, canine, ovine, or feline.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1E depict the generation of plasmid constructs and the biological sequences used. FIG. 1A depicts the construction of plasmid pMGM10. FIG. 1B depicts the construction of plasmid pMGM11. FIG. 1C depicts the codon-optimized slpA chimera nucleic acid sequence that was cloned into the plasmids pMGM10 and pMGM11. FIG. 1D depicts the amino acid sequence of the SlpA chimera polypeptide. FIG. 1E depicts the promoter sequences used in constructing the plasmids: fructooligosaccharides (Fos) promoter in plasmid pTRK848/pMGM11 and phosphoglycerate mutase (pgm) promoter pTRK882/pMGM10.

FIG. 8 provides a partial sequence of a plasmid used for a thyA directed integration of a SlpA chimeric protein encoding sequence into a bacterial genome and concomitantly insertionally inactivates thyA in *Lactobacillus acidophilus*.

FIG. 9 provides a partial sequence of a plasmid used for double homologous recombination-based system for replacing a thyA gene in a bacterial chromosome with a Slp A chimeric protein encoding sequence and a YtvA fluorescent reporter encoding sequence in *Lactobacillus acidophilus*.

DETAILED DESCRIPTION OF THE INVENTION

Figure 1A:
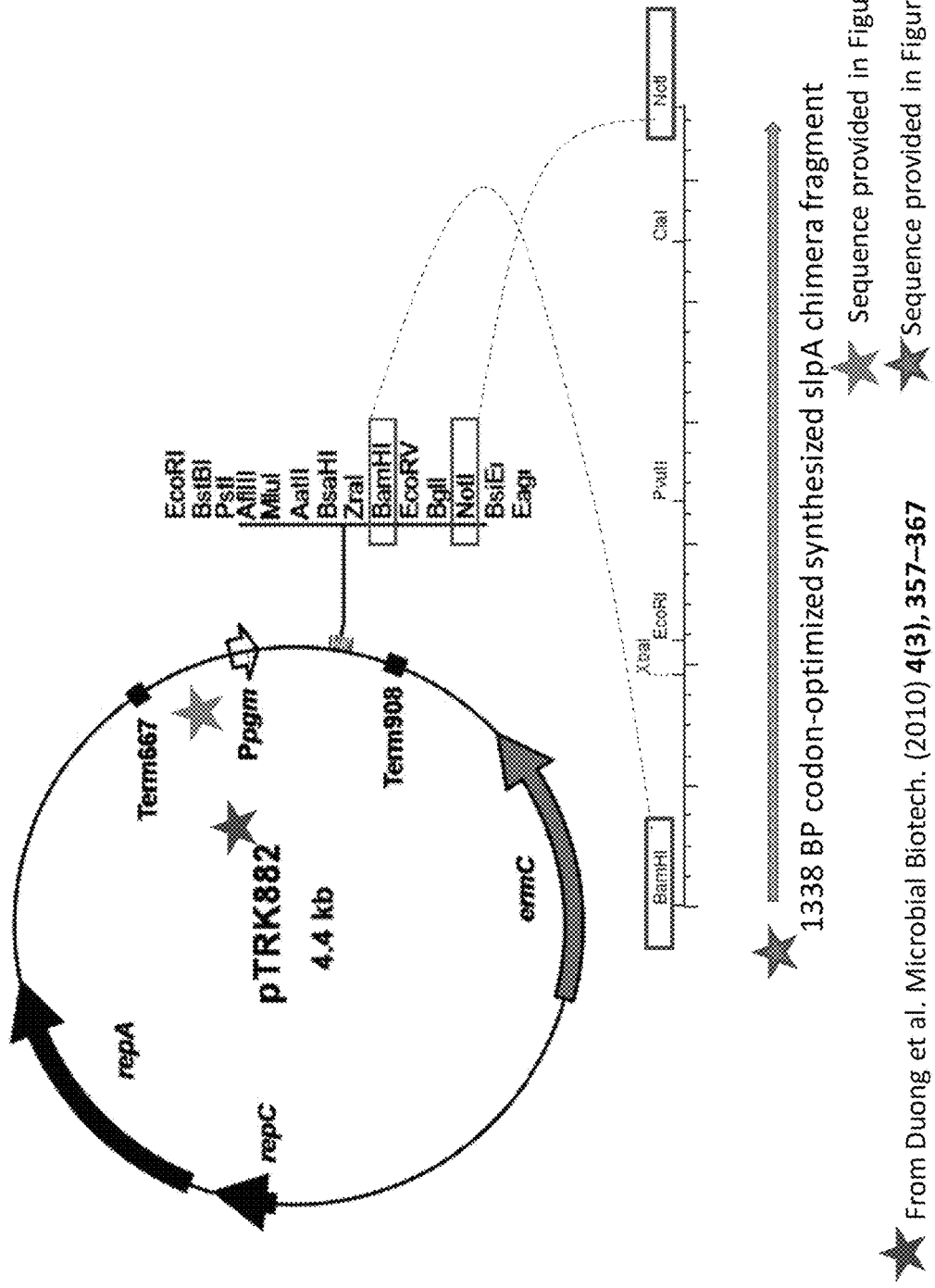
Figure 1B:
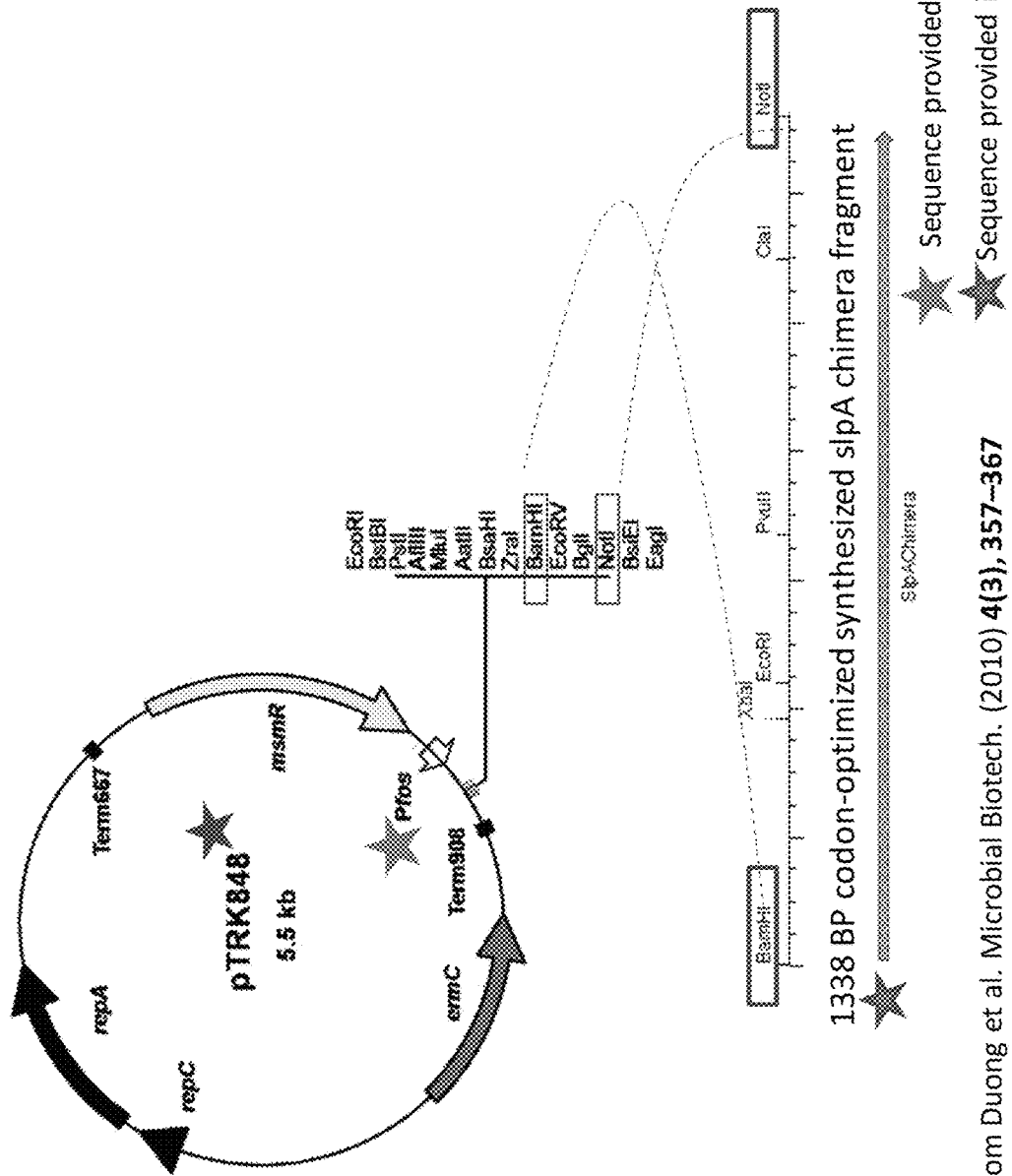
Figure 1E:
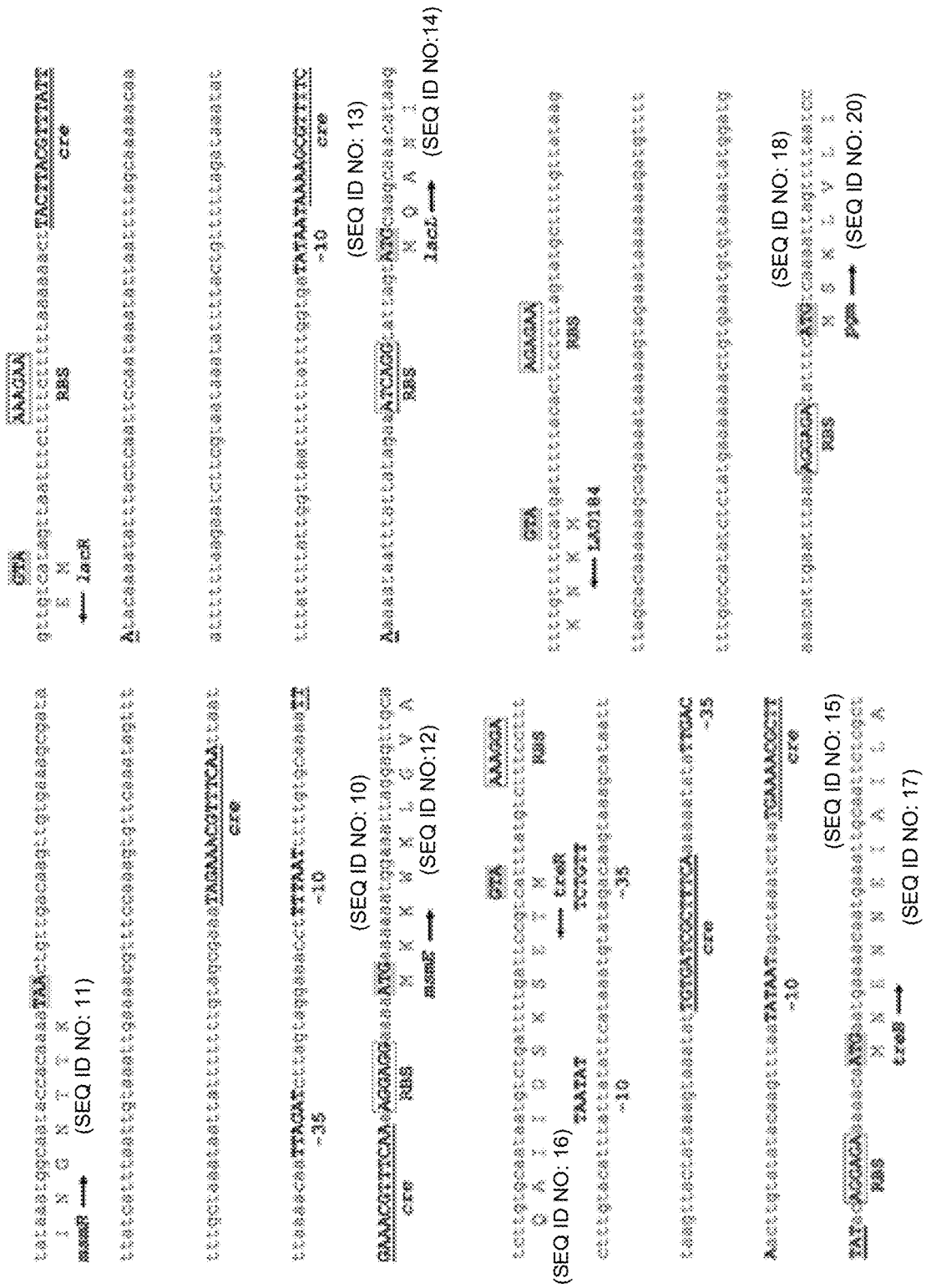

The invention provides a probiotic bacteria (e.g., *Lactobacillus, Lactococcus*) expressing the *Clostridium difficile* surface protein SlpA, or a fragment or chimeric polypeptide thereof, and its use for colonizing the gut or digestive tract of a subject. The invention also provides a method of treating or preventing *Clostridium difficile* infection and colonization. The invention features use of the probiotic bacteria of the invention for the replacement of a gut microbiome associated with disease.

The invention is based, at least in part, on the discovery that expression of *Clostridium difficile* SlpA (e.g., chimeric SlpA), or fragment thereof, in *Lactobacillus* or *Lactococcus* is effective for colonizing the gut with the recombinant bacteria. It was also found that recombinant *Lactobacillus* protected the gut from virulent *Clostridium difficile* challenge. These findings indicate that administration of gut recombinantly expressing *Clostridium difficile* SlpA, or fragment thereof can be used to treat or prevent *Clostridium difficile* infection and colonization.

*Clostridium difficile*

*Clostridium difficile* is a gram-positive, anaerobic, spore-forming bacterium, and causes the antibiotic-associated diarrheal disease, *C. difficile* infection (CDI). It is also a leading cause of bacterial healthcare-associated infections in hospitals in the United States. Like many enteric pathogens, *Clostridium difficile* must associate with the intestinal mucosa to begin the process of host colonization.

Multiple *C. difficile* adhesins have been described, including the flagellin FliC, the flagellar cap protein FliD, fibronectin-binding proteins, a heat-shock protein, GroEL, the surface associated, heat-shock-induced adhesin, Cwp66, and the surface layer protein, SlpA. SlpA contains two biologically distinct entities, the high-molecular weight (HMW) and the low molecular weight (LMW) subunits, which are derived via Cwp84-mediated cleavage of a single precursor protein, and assemble on the bacterial surface into a paracrystalline lattice. The two subunits associate with high affinity through the N-terminus of the HMW protein and the C-terminus of the LMW protein.

Cwp66 and SlpA are encoded by two genes in a 17-gene cluster that encodes many surface-associated proteins. Such S-layer proteins (SLPs) provide structural integrity to the cells, act as molecular sieves, bind to host tissues and extracellular matrix proteins, and contribute to host cell adhesion and immune evasion.

Surface-Layer Protein A (SlpA)

Many gram-positive bacteria including *C. difficile* possess a surface-layer that covers the peptidoglycan-rich cell wall. This "S-layer" consists of many proteins that form a paracrystalline lattice around the bacterial cell. The most abundant S-layer protein in *C. difficile* is SlpA, a major contributor of adhesion to, and colonization of, intestinal epithelial cells. (Merrigan et al. PLoS ONE 8(11): e78404). Individual subunits of the protein (varying in sequence between strains) mediated host-cell attachment to different extents. Pre-treatment of host cells with crude or purified SlpA subunits, or incubation of vegetative bacteria with anti-SlpA antisera significantly reduce *C. difficile* attachment. SlpA-mediated adherence-interference correlates with the attachment efficiency of the strain from which the protein was derived, with maximal blockage observed when SlpA is derived from highly adherent strains. In addition, SlpA-containing preparations from a non-toxigenic strain effectively blocked adherence of a phylogenetically distant, epidemic-associated strain, and vice-versa. Taken together, these results suggest that SlpA plays a major role in *C. difficile* infection, and that it may represent an attractive target for interventions aimed at abrogating gut colonization by this pathogen.

Therapeutic Compositions

The invention features probiotic bacteria expressing *Clostridium difficile* SlpA or fragment thereof (e.g., chimeric SlpA). In particular, *Clostridium difficile* SlpA, or fragment thereof, is expressed in *Lactoccocus* (e.g., *Lactoccocus lactis*) or *Lactobacillus* cells (e.g., *Lactobacillus acidophilus* or *Lactobacillus casei*). In additional embodiments, one or more strains of probiotic bacteria expressing a chimeric SlpA polypeptide are administered or formulated as a therapeutic composition. In certain embodiments, the SlpA expressed is a chimeric SlpA comprising a *C. difficile* SlpA variable domain and *Lactobacillus* (e.g., *Lactobacillus acidophilus* or *Lactobacillus casei*) SlpA cell wall binding domain. The SlpA additionally includes a bacterial secretion signal that is appropriate for surface expression in its host cell (e.g., *Lactoccocus, Lactobacillus, Lactobacillus acidophilus* or *Lactobacillus casei*). In various embodiments, the invention also includes nucleic acid molecules and vectors encoding a chimeric SlpA polypeptide. Vectors encoding the chimeric SlpA polypeptide can be used to direct or regulate the expression of the chimeric SlpA by the cell (see e.g., Duong et al., Microbial Biotechnology 2010, 4(3): 357-367 which is herein incorporated in its entirety by reference). Such vectors contain one or more origin of replication sequences that can be used by a bacterial cell, promoter sequences for expression in a bacterial cell (e.g., constitutive or inducible), genetic markers for selection (e.g., antibiotic resistance); origin of transfer sequences for bacterial conjugation (e.g., traJ), and may also be codon optimized for protein expression.

Alternatively, nucleic acid sequences encoding chimeric SlpA may be integrated into the *Lactobacillus* or *Lactococ-*

*cus* genome. In certain embodiments, nucleic acid sequences encoding the chimeric SlpA can be integrated into the *Lactobacillus* or *Lactococcus* genome through recombination between vectors comprising the nucleic acid sequence encoding the chimeric SlpA poly peptide and bacterial chromosome. Such techniques are well known in the art (see e.g., Leenhouts, et al., Appl. Environ. Microbiol. 1989, 55(2): 394-400, and Gaspar, et al., Appl. Environ. Microbiol. 2004, 70(3): 1466-74 which are herein incorporated in their entirety by reference).

Probiotic strains may also be engineered with auxotrophic selection, for example requiring thiamine or thymine supplementation for survival.

Methods of the Invention

The present invention provides methods of treating diseases or symptoms thereof associated with the presence of one or more undesirable bacteria in the gut of a subject. Accordingly, the invention provides compositions and methods for treating a subject having or at risk of developing a disease associated with undesirable changes in the gut microbiome, the method involving administering a therapeutically effective amount of a composition comprising a probiotic bacteria of the invention to a subject (e.g., a mammal, such as a human). In particular, the compositions and methods of the invention are effective for treating or preventing *Clostridium difficile* infection, colonization, or diseases and symptoms thereof (e.g., diarrhea). Without being bound to theory, *Lactobacillus* or *Lactococcus* expressing *Clostridium difficile* SlpA or fragment thereof (e.g., chimeric SlpA) colonize the gut and compete with *Clostridium difficile* for binding and colonization. Accordingly, the method includes the step of administering to a mammal a therapeutic amount of an amount of a composition comprising one or more probiotic bacteria strains of the invention sufficient to treat the disease or disorder or symptom thereof, under conditions such that the disease or disorder is treated.

Identifying a subject in need of treatment for a disease associated with the gut microbiome can be in the judgment of a health care professional and can be subjective (e.g. opinion) or objective (e.g. measurable by a test or diagnostic method). In certain embodiments, the subject has undergone or is undergoing treatment with antibiotics. As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of a composition comprising the probiotic bacteria of the invention to a subject (e.g., human) in need thereof. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider. The compositions herein may be also used in the treatment of any other disorders in which a microbial imbalance in the digestive tract may be implicated.

Methods of Delivery

Compositions comprising the probiotic bacteria of the invention may be administered orally, rectally, or enterally. Preferably compositions administered to a subject in tablet form, by feeding tube, by enema, or by colonoscopy. Preferably, the probiotic bacteria of the invention are diluted in a suitable excipient (e.g., saline solution). An effective dose may include $10^6$-$10^9$ colony forming units of bacteria per day).

Expression of Recombinant Polypeptides

In order to express the fusion protein of the invention, DNA molecules obtained by any of the methods described herein or those that are known in the art, can be inserted into appropriate expression vectors by techniques well known in the art. For example, a double stranded DNA can be cloned into a suitable vector by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding an SlpA chimeric polypeptide operatively linked to regulatory sequences, e.g., promoter sequences, terminator sequences, and the like, as defined herein. Recombinant vectors which allow for expression of the genes or nucleic acids included in them are referred to as "expression vectors."

In some of the molecules of the invention described herein, one or more DNA molecules having a nucleotide sequence encoding one or more polypeptides of the invention are operatively linked to one or more regulatory sequences, which are capable of integrating the desired DNA molecule into a prokaryotic host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

After the introduction of one or more vector(s), host cells are usually grown in a selective medium, which selects for the growth of vector-containing cells. Expression of recombinant proteins can be detected by immunoassays including Western blot analysis, immunoblot, and immunofluorescence. Purification of recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

Kits

The invention provides kits for colonizing probiotic bacteria of the invention in the gut of a host. The invention also provides kits for the treatment or prevention of *Clostridium difficile* infection or colonization. In particular embodiments, the kit comprises a sterile container which contains a therapeutic or prophylactic composition comprising the probiotic bacteria of the invention; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

The kit preferably contains instructions that generally include information about the use of the composition for the expansion of the microbial consortia in the gut of the subject. The kit further contains precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Probiotic Bacterial Strains Expressing Chimeric SlpA are Effective at Gut Colonization and Protecting Against *C. difficile* Challenge Developing novel interventions that avoid the use of antibiotics is important in the treatment of *C. difficile* infection (CDI). Many gram-positive bacteria including *C. difficile* possess a surface-layer that covers the peptidoglycan-rich cell wall. This "S-layer" consists of many proteins that form a paracrystalline lattice around the bacterial cell. Surface layer protein A (SlpA), an adhesin and a major component of the cell surface layer (or S-layer) of *C. difficile*, facilitates gut colonization. Novel probiotic organisms were designed and engineered to express *C. difficile* SlpA on their cell surface (FIGS. 1A-1E). Without being bound to a particular theory, the engineered probiotic colonizes gut niches specifically occupied by virulent infecting *C. difficile* strains, thus preventing disease.

Figure 2:
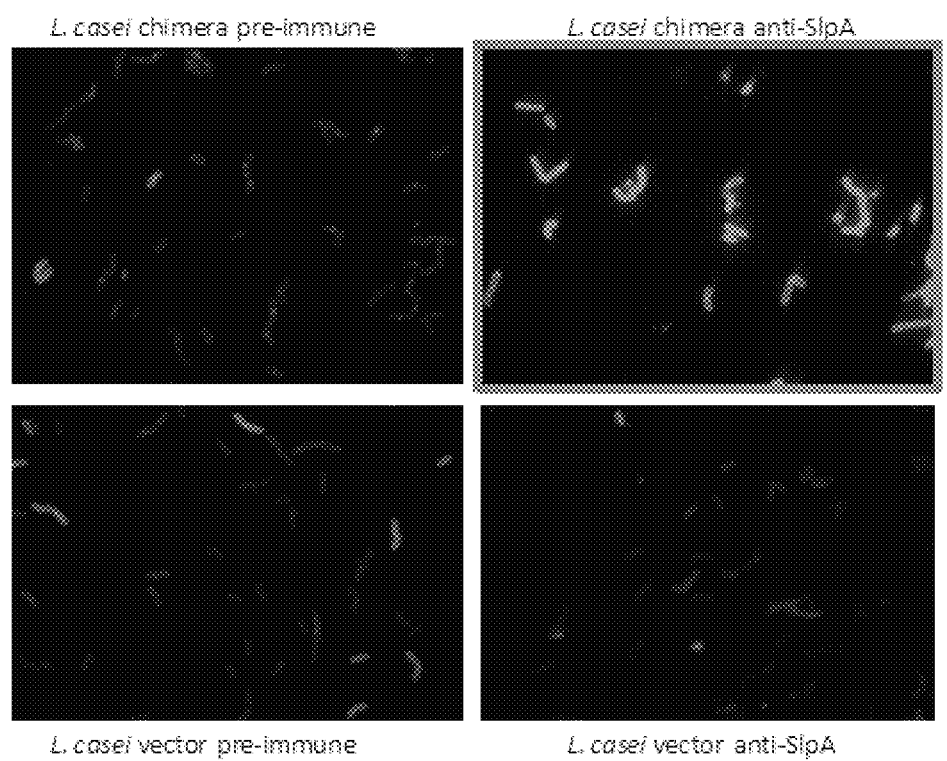
FIG. 2 are immunofluorescence images showing the surface expression of C. difficile SlpA in Lactobacillus casei compared to pre-immune serum and vector only controls.

A chimeric SlpA polypeptide was created that included *C. difficile* SlpA sequences for bacterial adherence. The chimeric SlpA polypeptide was designed with a *L. acidophilus* cell-wall binding domain and secretion signal sequence and the host-cell binding domain of *C. difficile*. Plasmid vectors were constructed to express the slpA chimera either constitutively or in response to a fructose oligosaccharide inducer. Plasmid vectors encoding SlpA chimeras were designed and introduced into probiotic bacterial strains *Lactoccocus lactis* and *Lactobacillus acidophilus* via three methods, electroporation, bacterial conjugation (pMTL82151 with pTRK848 comprising traJ; pMTL82151 with pTRK882 comprising traJ), and protoplasting. Transformants were assessed for stable carriage of introduced plasmids, and tested for SlpA surface expression. Western blot analysis and cell surface immunofluorescence showed that the chimeric SlpA was expressed by the probiotic bacterial cells (FIG. 2).

Figure 3:
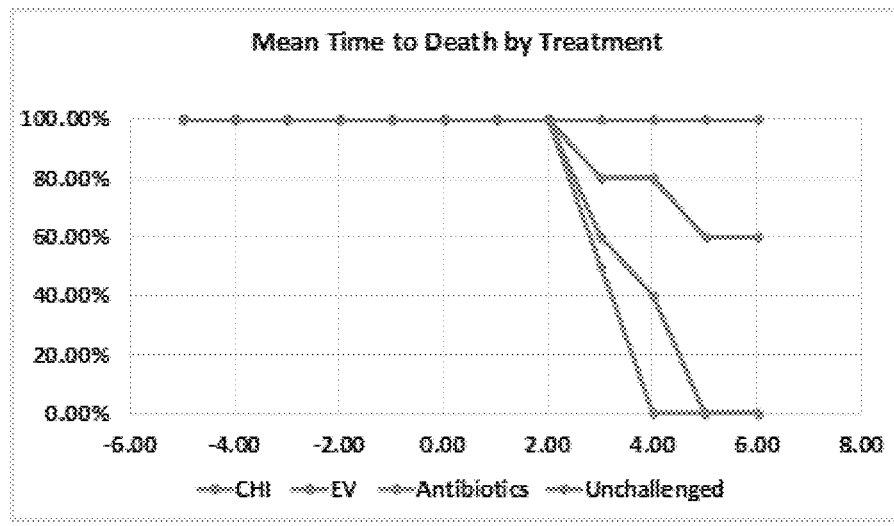
FIG. 3 is a graph showing mean time to death in Syrian Golden hamsters challenged with virulent Clostridium difficile and treated with recombinant Lactobacillus expressing a chimeric SlpA (CHI) or Lactobacillus carrying an empty vector ( fluorescent reporter encoding sequence. *Lactobacillus casei* and *Lactobacillus acidophilus* specific constructs were made. The thyA gene encodes an essential enzyme thymidylate synthase (ThyA). The YtvA is an anaerobic fluorescent protein used to confirm transformation of *Lactobacillus* sp and monitor colonization. A gene catP encodes an enzyme Chloramphenicol acetyltransferase, which is an effector of chloramphenicol resistance in bacteria. A region including an oriR and a repA$^{ts}$ genes constitutes a temperature sensitive broad host replicon based on pWVO1 plasmid.

To test the ability of the recombinant bacteria expressing the chimeric SlpA to occlude *C. difficile* competitively, a study was performed in Syrian Golden hamsters (FIG. 3). Animals were treated with recombinant *Lactobacillus* expressing a chimeric SlpA or *Lactobacillus* carrying an empty vector. Another group of animals underwent treatment with antibiotics. animals that were administered *Lactobacillus* expressing chimeric SlpA showed extended survival and overall survival at the conclusion of the experiment. By comparison, none of the animals that were treated with antibiotics or administered *Lactobacillus* with empty vector survived to the end of the experiment. All animals that were not challenged with virulent *C. difficile* survived to the end of the experiment. These results show that *Lactobacillus* expressing the chimeric SlpA colonized the gut and was able to protect against virulent *C. difficile* challenge. Thus, this indicates that administration of probiotic bacteria expressing chimeric SlpA has the potential to be an effective treatment or preventative for *C. difficile* infection and/or colonization.

Figure 4:
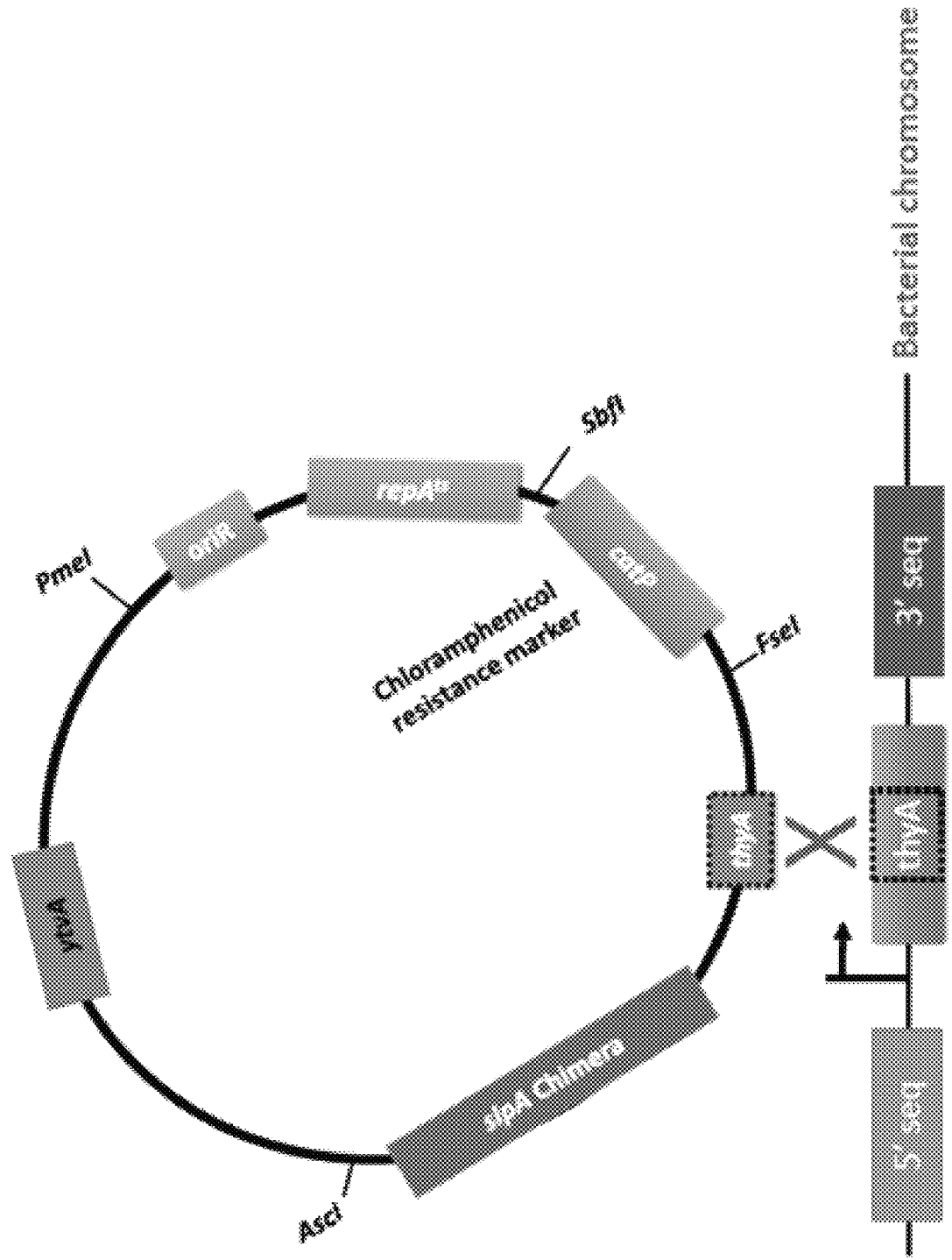
Figure 5:
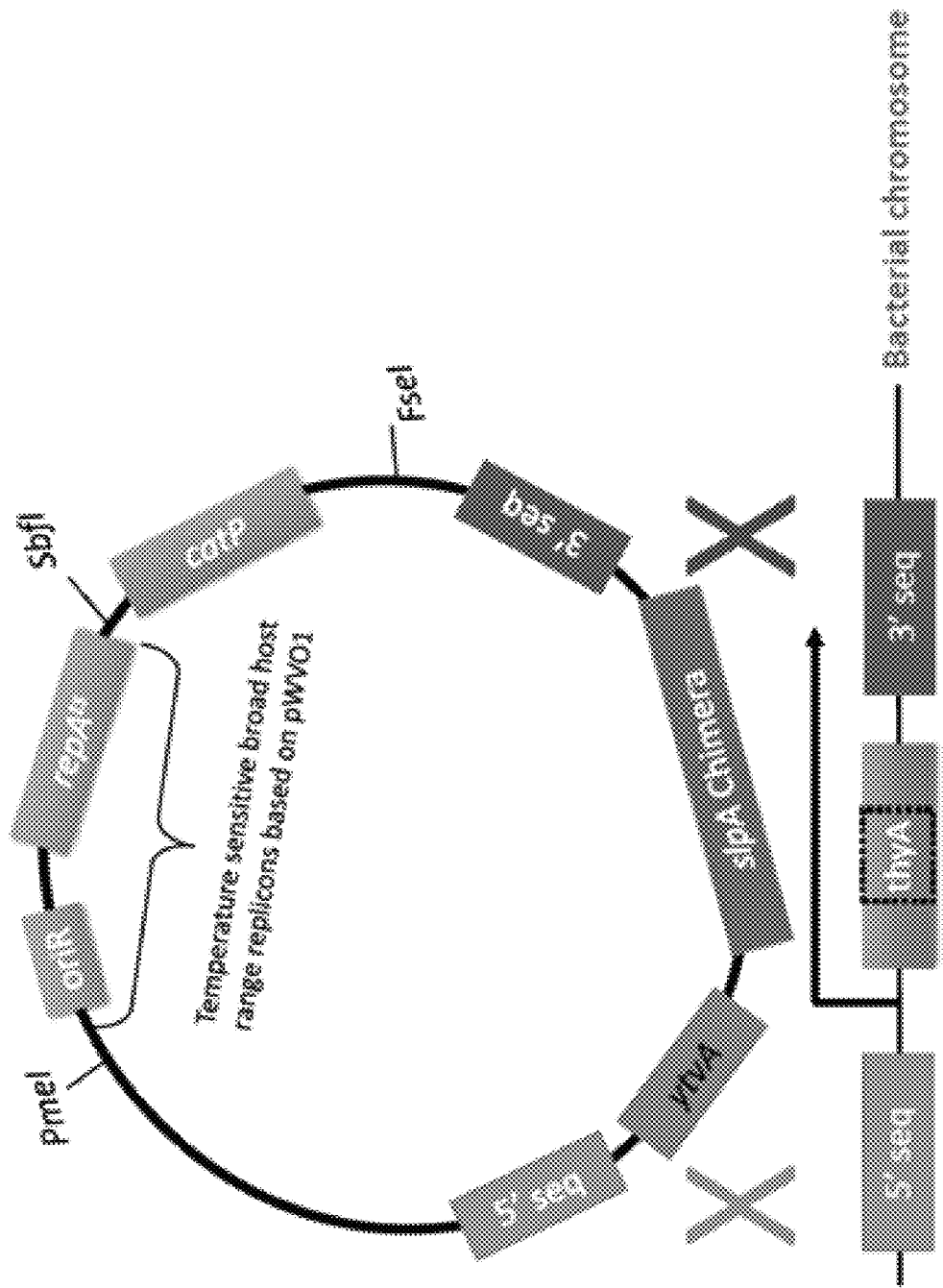

Example 2: A Chimeric SlpA Polynucleotide can be Integrated into the *Lactobacillus* Genome Probiotic organisms can include biocontainment features for eventual clinical use and, concomitantly, obviating the requirement of antibiotics for in vivo plasmid maintenance and stable SlpA expression. The SlpA expression may also be controlled. The biological containment can be achieved via a two-step mechanism, where both SlpA expression and *Lactobacillus* sp. survival can be controlled. Novel vectors were designed to allow probiotic organisms to express chimeric SlpA stably and under control (FIGS. 4 and 5). In one embodiment, the nucleic acid sequence encoding a chimeric SlpA peptide can be integrated into a bacterial chromosome to allow stability of SlpA expression in the absence of selection pressure. The chimeric SlpA expression can be expressed under the control of a fructo-oligosaccharide (FOS) promoter. FOSs are well-tolerated, safe and widely-used supplements in humans and agriculturally-relevant animals.

Probiotic organisms expressing the chimeric SlpA protein, such as the lactic acid bacterium, including both *L. casei* and *L. acidophilus*, can be genetically modified such that complete lethality of the probiotic organisms occurs in the absence of thymine supplementation. This "thymineless death" is predicated on the absolute requirement of deoxythymidine triphosphate (dTTP) for DNA synthesis in all living organisms. Of the two pathways for dTTP synthesis in most bacteria, the de novo pathway involves conversion of dUMP to dTMP by the essential enzyme thymidylate synthase (ThyA). The less-used "salvage" pathway involves the conversion of supplemented thymidine into dTMP by thymidine kinase. dTMP is then converted to dTTP. Disruption or mutation of thyA in bacteria results in immediate auxotrophy and, in vitro, can be tolerated only by addition of exogenous thymidine that is utilized by the salvage pathway. Withdrawal of thymidine results in rapid, total cell death. Free thymidine is not abundant or bio-available in vivo (in the gut), and is unable to support growth of thyA auxotrophs. Therefore, the probiotic organisms with thyA gene disrupted will necessarily be lost from the gut unless continually administered.

Figure 6:
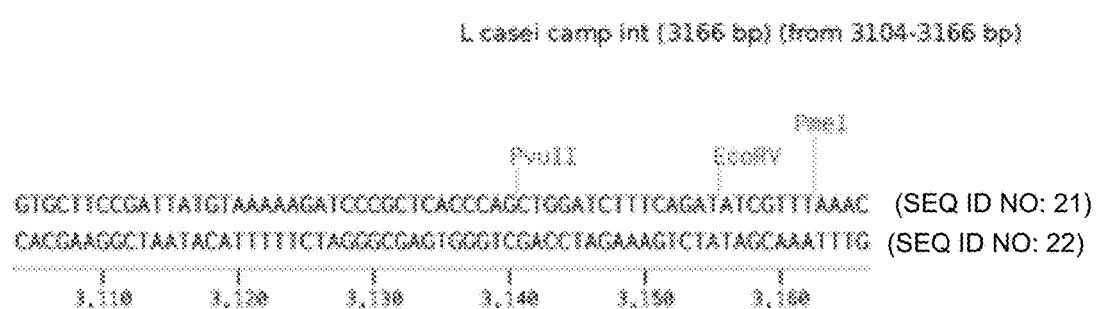
FIG. 6 provides a partial sequence of a plasmid used for a thyA directed integration of a SlpA chimeric protein encoding sequence into a bacterial genome and concomitantly insertionally inactivates thyA in *Lactobacillus casei*.
Figure 8:
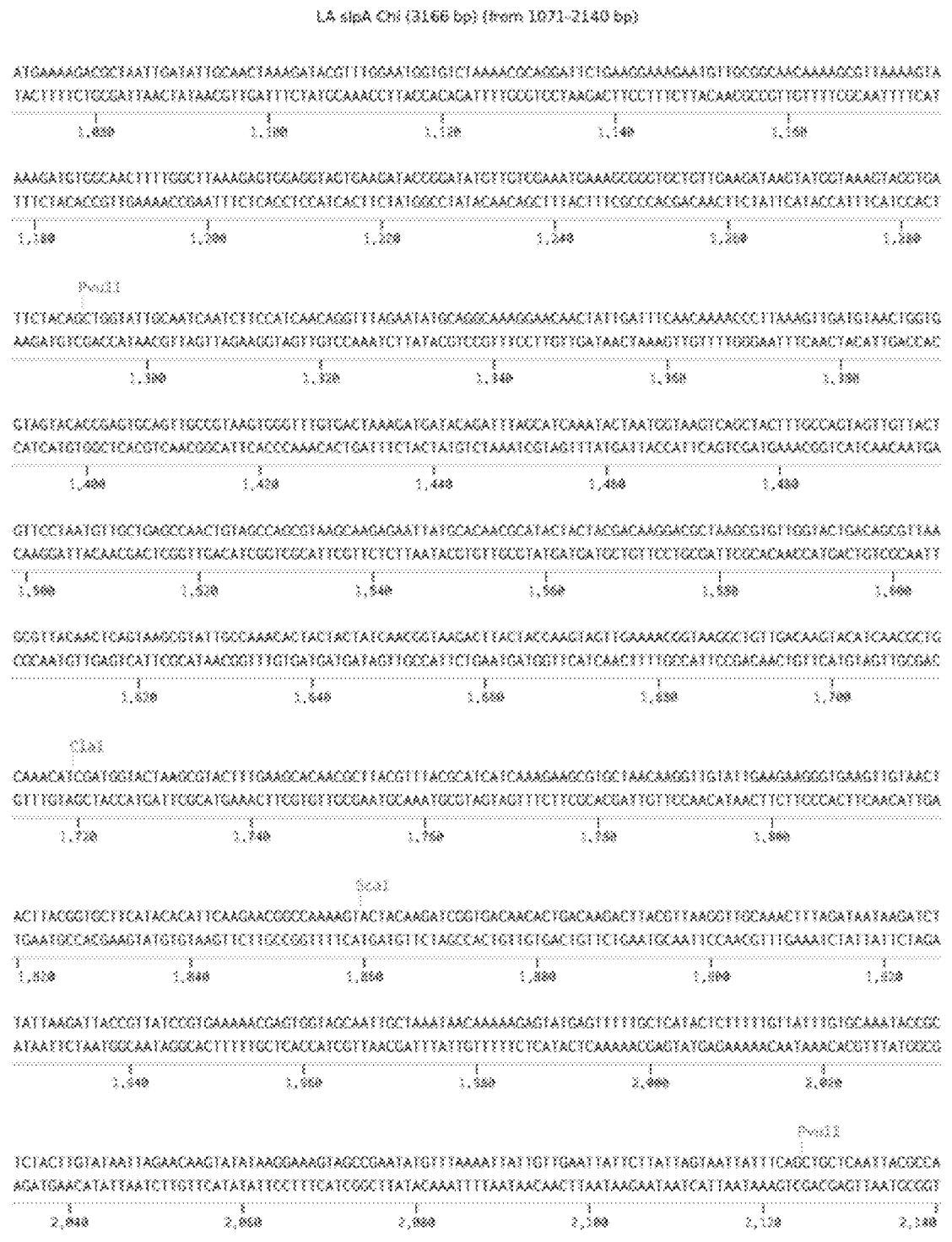
Figure 8:
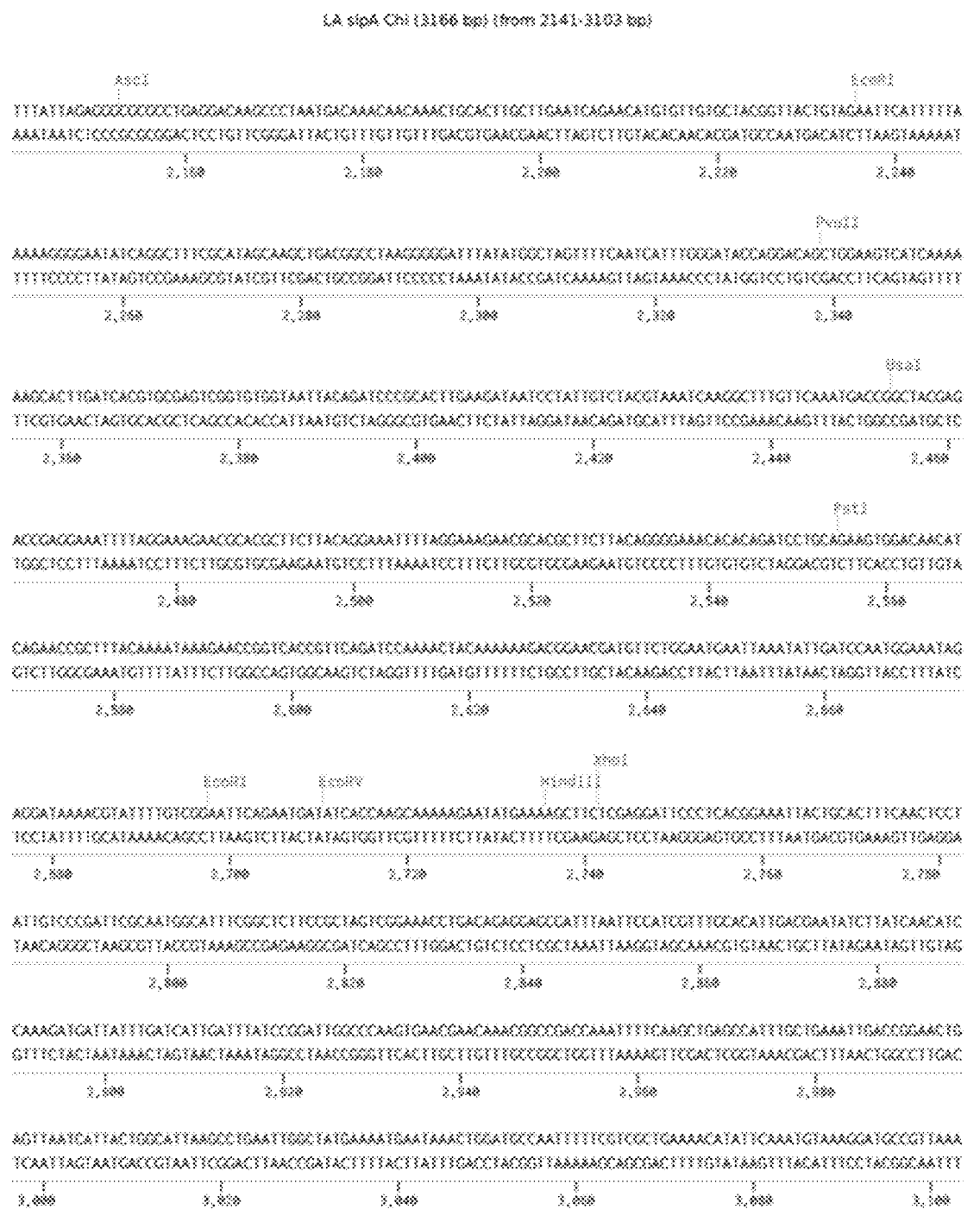

The nucleic acid sequence encoding the chimeric SlpA can be integrated into the *Lactobacillus* sp. through a single homologous recombination at a single site (FIG. 4) or a double homologous recombination (FIG. 5). For the single homologous recombination, one vector is constructed for each species. Thus, a vector is constructed for specific use in *L. casei*, such that the vector includes a nucleic acid sequence that is identical to a nucleic acid sequence of a fragment of the thyA gene in *L. casei*. Another vector is constructed for specific use in *L. acidophilus*, such that the vector includes a nucleic acid sequence that is identical to a nucleic acid sequence of a fragment of the thyA gene in *L. acidophilus*. The sequence of the vector for the specific use in *L. casei* for single recombination is shown in FIG. 6 and the sequence of the vector for the specific use in *L. acidophilus* for single recombination is shown in FIG. 8.

Figure 7:
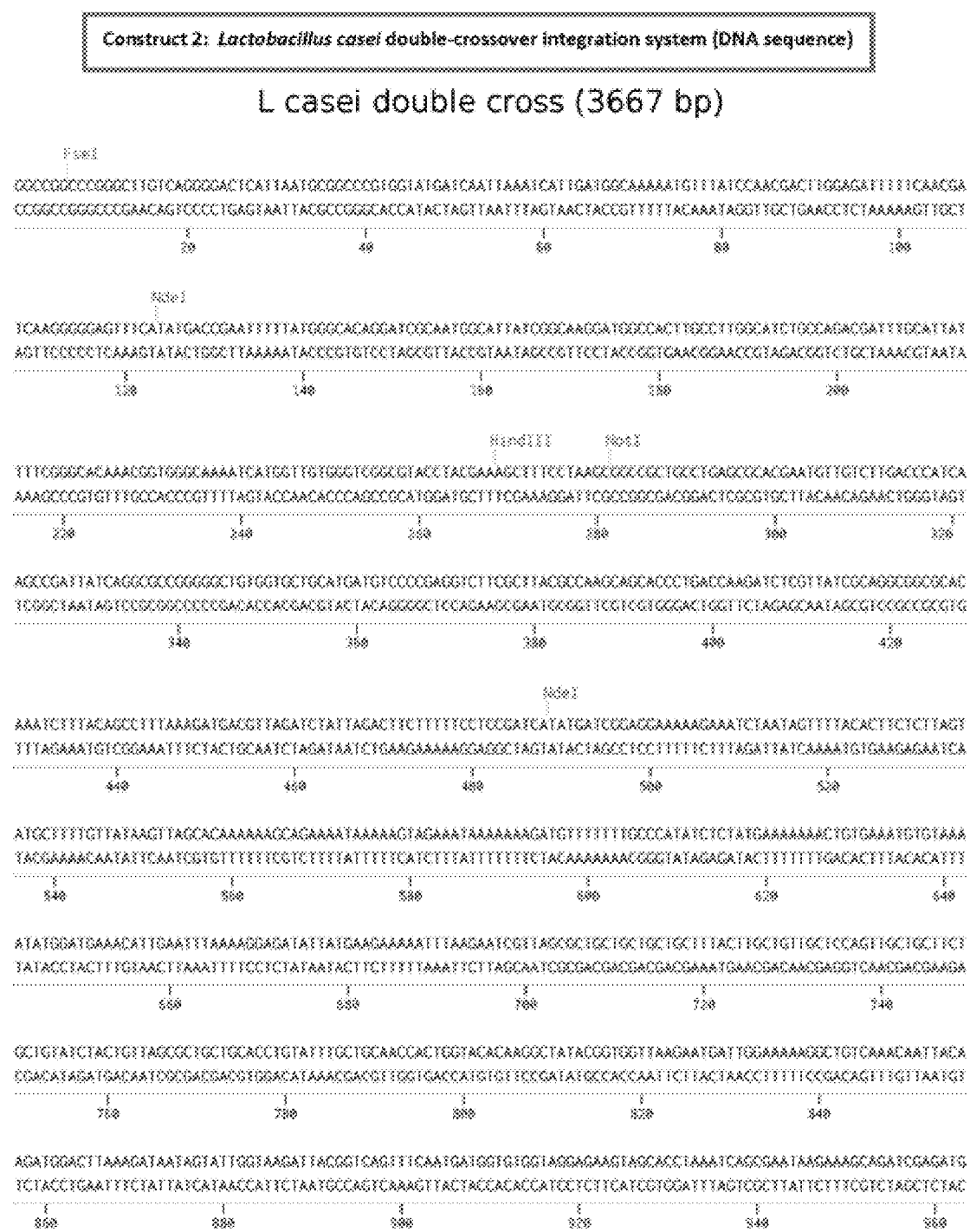
FIG. 7 provides a partial sequence of a plasmid used for double homologous recombination-based system for replacing a thyA gene in a bacterial chromosome with a Slp A chimeric protein encoding sequence and a YtvA fluorescent reporter encoding sequence in *Lactobacillus casei*.
Figure 9:
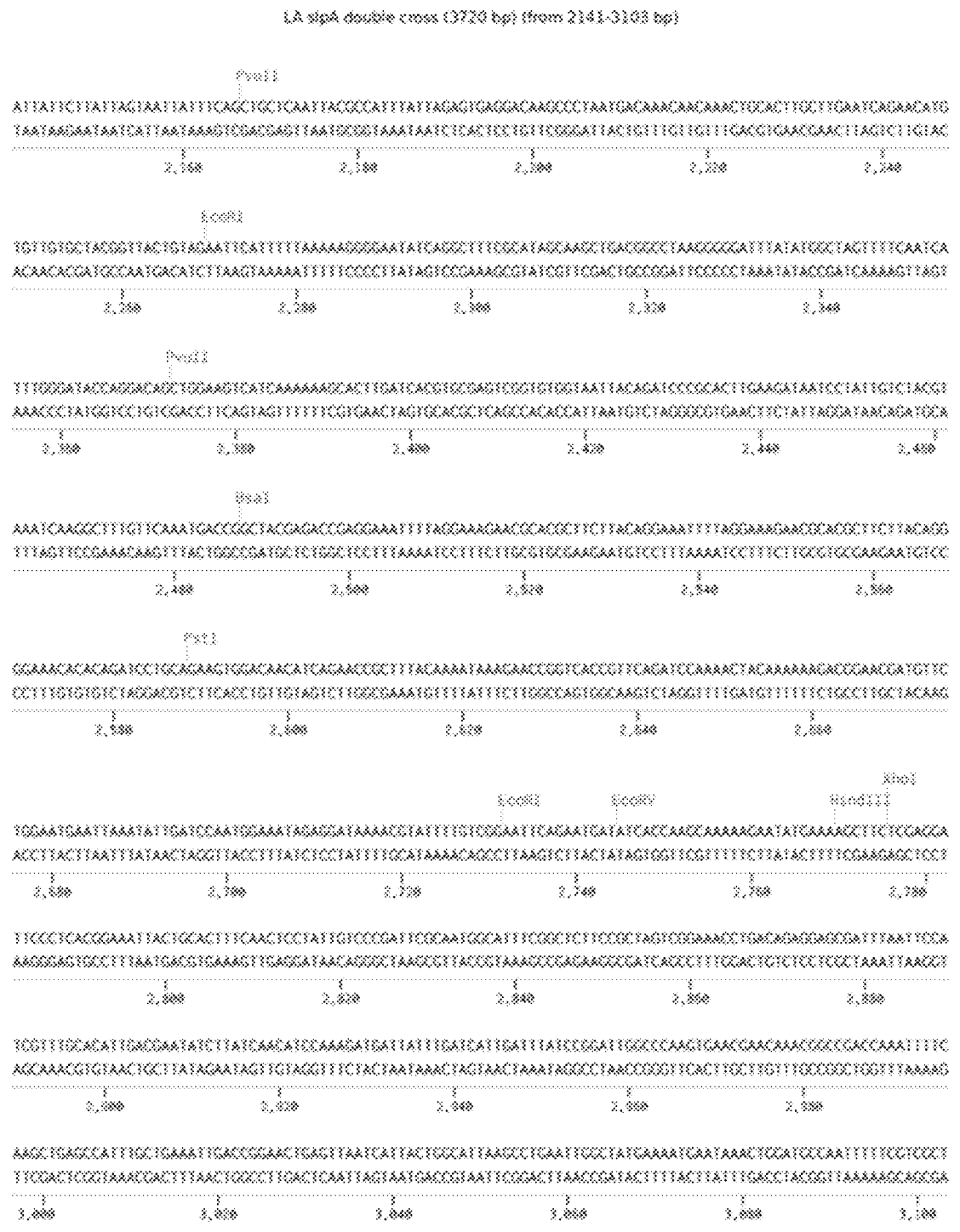

For the double homologous recombination, one vector is constructed for each species. Thus, a vector is constructed for specific use in *L. casei*, such that the vector includes a first nucleic acid sequence that is identical to a nucleic acid sequence of a fragment located at the 5' of the thyA gene in *L. casei* and a second nucleic acid sequence that is identical to a nucleic acid sequence of a fragment located at the 3' of the thyA gene in *L. casei*. Another vector is constructed for specific use in *L. acidophilus*, such that the vector includes a first nucleic acid sequence that is identical to a nucleic acid sequence of a first fragment located at the 5' of the thyA gene in *L. acidophilus* and a second nucleic acid sequence that is identical to a nucleic acid sequence of a second fragment located at the 3' of the thyA gene in *L. acidophilus*. The sequence of the vector for the specific use in *L. casei* for double recombination is shown in FIG. 7 and the sequence of the vector for the specific use in *L. acidophilus* for double homologous recombination is shown in FIG. 9.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A host cell comprising a nucleic acid sequence optimized for expression in *Lactococcus, Lactococcus lactis, Lactobacillus, Lactobacillus acidophilus*, or *Lactobacillus casei*, wherein the nucleic acid sequence is SEQ ID NO:5 and encodes a polypeptide comprising a bacterial secretion signal, a *C. difficile* Surface layer protein A (SlpA) variable domain, and a *Lactobacillus* SlpA cell wall binding domain.

2. The host cell of claim 1, wherein the polypeptide has the amino acid sequence SEQ ID NO: 4.

3. The host cell of claim 1, wherein the cell is selected from the group consisting of a *Lactococcus, Lactococcus lactis, Lactobacillus, Lactobacillus acidophilus*, or *Lactobacillus casei* cell.

4. The host cell of claim 1, wherein the nucleic acid molecule is integrated into the chromosome of the cell.

5. A vector comprising a nucleic acid sequence optimized for expression in *Lactococcus, Lactococcus lactis, Lactobacillus, Lactobacillus acidophilus*, or *Lactobacillus casei*, wherein the nucleic acid sequence is SEQ ID NO:5 and encodes a polypeptide comprising a bacterial secretion signal, a *C. difficile* Surface layer protein A (SlpA) variable domain, and a *Lactobacillus* SlpA cell wall binding domain.

6. The vector of claim 5, wherein the polypeptide has the amino acid sequence SEQ ID NO: 4.

7. The vector of claim 5, wherein the vector is a *Lactococcus, Lactobacillus, Lactobacillus acidophilus*, or *Lactobacillus casei* expression vector, and wherein the vector comprises a *Lactococcus* or *Lactobacillus* origin of replication.

8. The vector of claim 5, comprising a first sequence identical to a sequence of a first fragment in a *Lactobacillus* genome, wherein the first fragment is located at the 5' or 3' terminus of a thyA gene, or within the thyA gene of *Lactobacillus*, and a second sequence identical to a second fragment in the *Lactobacillus* genome, wherein the second fragment is located at the 5' or 3' terminus of the thyA gene.

* * * * *